US009528979B2

(12) United States Patent
Haick et al.

(10) Patent No.: US 9,528,979 B2
(45) Date of Patent: Dec. 27, 2016

(54) BREATH ANALYSIS OF PULMONARY NODULES

(71) Applicants: Technion Research and Development Foundation Ltd., Haifa (IL); Tel Hashomer Medical Research, Infrastructure and Services Ltd., Ramat Gan (IL)

(72) Inventors: Hossam Haick, Haifa (IL); Nir Peled, Hod Hasharon (IL)

(73) Assignees: TECHNION RESEARCH AND DEVELOPMENT FOUNDATION LTD., Haifa (IL); TEL HASHOMER MEDICAL RESEARCH, INFRASTRUCTURE AND SERVICES LTD., Ramat Gan (IL)

( * ) Notice: Subject to any disclaimer, the term of this patent is extended or adjusted under 35 U.S.C. 154(b) by 1078 days.

(21) Appl. No.: 13/678,126

(22) Filed: Nov. 15, 2012

(65) Prior Publication Data
US 2013/0150261 A1 Jun. 13, 2013

Related U.S. Application Data

(60) Provisional application No. 61/560,008, filed on Nov. 15, 2011.

(51) Int. Cl.
*G01N 33/497* (2006.01)
*G01N 33/00* (2006.01)

(52) U.S. Cl.
CPC ......... *G01N 33/497* (2013.01); *G01N 33/0034* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 4,772,559 A | 9/1988 | Preti | |
| 5,996,586 A | 12/1999 | Phillips | |
| 6,540,691 B1 | 4/2003 | Phillips | |
| 2008/0220984 A1 | 9/2008 | Bright | |
| 2010/0137733 A1 | 6/2010 | Wang | |
| 2012/0175571 A1* | 7/2012 | Sarkar | B82Y 30/00 252/582 |

FOREIGN PATENT DOCUMENTS

| | | |
|---|---|---|
| WO | 00/41623 | 7/2000 |
| WO | 03/014724 | 2/2003 |
| WO | 2004/008953 | 1/2004 |
| WO | 2006/112733 | 10/2006 |
| WO | 2007/086986 | 8/2007 |
| WO | 2008/151238 | 12/2008 |
| WO | 2009/004576 | 1/2009 |
| WO | 2009/066293 | 5/2009 |
| WO | 2009/118205 | 10/2009 |
| WO | 2009/144725 | 12/2009 |
| WO | 2010/064239 | 6/2010 |
| WO | 2010/079490 | 7/2010 |
| WO | 2010/079491 | 7/2010 |
| WO | 2011/083473 | 7/2011 |
| WO | 2012/023138 | 2/2012 |

OTHER PUBLICATIONS

Amann, A. et al., "Analysis of exhaled breath for screening of lung cancer patients. memo" 3(3):106-112 (2010).
Amann, A. et al., "Methodological issues of sample collection and analysis of exhaled breath" European Respiratory Society Monograph 49:96-114 (2010).
Amann, Anton et al., "Lung cancer biomarkers in exhaled breath" Expert Rev Mol Diagn 11(2):207-217 (2011).
Bajtarevic, Amel et al., "Noninvasive detection of lung cancer by analysis of exhaled breath" BMC Cancer 29(9):348 (2009).
Barash, Orna et al., "Classification of lung cancer histology by gold nanoparticle sensors" Nanomedicine 8(5):580-589 (2012).
Brust, Mathias et al., "Synthesis of thiolderivatizedgold nanoparticlesin a 2-phase liquid-liquid system" J. Chem. Soc. Chem. Commun. 1994 801-802 (1994).
Chen, Xing et al., "A study of an electronic nose for detection of lung cancer based on a virtual SAW gas sensors array and imaging recognition method" Meas. Sci. Technol. 16(8):1535-1546 (2005).
Chen, Xing et al., "A study of the volatile organic compounds exhaled by lung cancer cells in vitro for breath diagnosis" Cancer 110(4):835-844 (2007).
Di Natale, Corrado et al., "Lung cancer identification by the analysis of breath by means of an array of non-selective gas sensors. Biosensors and Bioelectronics" 18(10):1209-1218 (2003).
Dovgolevsky, E. et al., "Monolayer-Capped Cubic Platinum Nnoparticles for Sensing Nonpolar Analyst in Highly Humid Atmospheres" J. Phys. Chem. C 114:14042-14049 (2010).
Dragonieri, Silvano et al., "An electronic nose in the discrimination of patients with non-small cell lung cancer and COPD" Lung Cancer 64(2):166-170 (2009).
Feng, Xinliang et al., "Controlling the columnar orientation of C3-symmetric "superbenzenes" through alternating polar/apolar substitutents" Angew Chem Int Ed Engl 47(9):1703-1706 (2008).
Feng, Xinliang et al., "Supramolecular organization and photovoltaics of triangle-shaped discotic graphenes with swallow-tailed alkyl substituents" Adv Mater 20(14):2684-2689 (2008).
Feng, Xinliang et al., "Controlled Self-Assembly of C3-Symmetric Hexa-peri-hexabenzocoronenes with Alternating Hydrophilic and Hydrophobic Substituents in Solution, in the Bulk, and on a Surface" J Am Chem Soc 131(12):4439-4448 (2009).
Feng, Xinliang et al., "Towards high charge-carrier mobilities by rational design of the shape and periphery of discotics" Nature Mater 8(5):421-426 (2009).

(Continued)

*Primary Examiner* — Christopher M Gross
(74) *Attorney, Agent, or Firm* — Browdy and Neimark, PLLC

(57) ABSTRACT

The present invention provides a unique profile of volatile organic compounds as breath biomarkers for lung cancer. The present invention further provides the diagnosis, prognosis and monitoring of lung cancer or predicting the response to an anti-cancer treatment through the detection of the unique profile of volatile organic compounds indicative of lung cancer at its various stages.

19 Claims, 12 Drawing Sheets

(56) References Cited

OTHER PUBLICATIONS

Filipiak, Wojciech et al., "Release of volatile organic compounds (VOCs) from the lung cancer cell line CALU-1 in vitro" Cancer Cell Int 8:17 (2008).
Gasper, Elvira M. et al., "Organic metabolites in exhaled human breath—A multivariate approach for identification of biomarkers in lung disorders" J Chromatography A 1216(14):2749-2756 (2009).
Gordon, S. M. et al., "Volatile organic compounds in exhaled air from patients with lung cancer" Clin Chem 31(8):1278-1282 (1985).
Hakim, M. et al., "Diagnosis of head-and-neck cancer from exhaled breath" Br J Cancer 104(10):1649-1655 (2011).
Hakim, Meggie et al., "Volatile Organic Compounds of Lung Cancer and Possible Biochemical Pathways" Chem Rev Epub ahead of print: Sep. 19, 2012 (2012).
Hostetler, Michael J. et al., "Alkanethiolate Gold Cluster Molecules with Core Diameters from 1.5 to 5.2 nm: Core and Monolayer Properties as a Function of Core Size" Langmuir 14(1):17-30 (1998).
Hsu, et al. "Cancer cell metabolism: Warburg and beyond" Cell 134(5):703-707 (2008).
Ligor, T. et al., "The analysis of healthy volunteers' exhaled breath by the use of solid-phase microextraction and GC-MS" J Breath Res 2:04006 (8pp) (2008).
Ligor, Magdalena et al., "Determination of volatile organic compounds in exhaled breath of patients with lung cancer using solid phase microextraction and gas chromatography mass spectrometry" Clin Chem Lab Med 47(5):550-560 (2009).
Lindinger, W. et al., "On-line monitoring of volatile organic compounds at pptv levels by means of proton-transfer-reaction mass spectrometry (PTR-MS) medical applications, food control and environmental research" Mass Spectrom Ion Process 173(3):191-241 (1998).
Lindinger, Werner et al., "Environmental, food and medical applications of proton-transfer-reaction mass spectrometry (PTR-MS)" Adv Gas Phase Ion Chem 4:1-35 (2001).
Machado, Roberto F. et al., "Detection of lung cancer by sensor array analyses of exhaled breath" Am J Respir Crit Care Med 171(11):1286-1291 (2005).
Mazzone, Peter J. et al., "Diagnosis of lung cancer by the analysis of exhaled breath with a colorimetric sensor array" Thorax 62(7):565-568 (2007).
Miekisch, Wolfram et al., "Diagnostic potential of breath analysis—focus on volatile organic compounds" Clin Chim Acta 347(1-2):25-39 (2004).
O'Neill, H. J. et al., "A computerized classification technique for screening for the presence of breath biomarkers in lung cancer" Clin Chem 34(8):1613-1617 (1998).
Ouyang, Gangfeng et al. "SPME in environmental analysis" Anal Bioanal Chem 386(4):1059-1073 (2006).
Peled, Nir et al., "Non-invasive breath analysis of pulmonary nodules" J Thorac Oncol 7(10):1528-1533 (2012).
Peng, Gang et al., "Detecting simulated patterns of lung cancer biomarkers by random network of single-walled carbon nanotubes coated with nonpolymeric organic materials" Nano Lett 8(11):3631-3635 (2008).
Peng, Gang et al., "Diagnosing lung cancer in exhaled breath using gold nanoparticles" Nature Nanotech 4(10):669-673 (2009).
Peng, G. et al., Detection of lung, breast, colorectal, and prostate cancers from exhaled breath using a single array of nanosensors. Br J Cancer 103(4):542-551 (2010).
Phillips, Michael et al., "Volatile organic compounds in breath as markers of lung cancer: a cross-sectional study" Lancet 353(9168):1930-1933 (1999).
Phillips, Michael et al., "Detection of lung cancer with volatile markers in the breath" Chest 123(6):2115-2123 (2003).
Phillips, Michael et al., "Prediction of lung cancer using volatile biomarkers in breath" Cancer Biomark 3(2):95-109 (2007).
Phillips, Michael et al., "Detection of lung cancer using weighted digital analysis of breath biomarkers" Clin Chim Acta 393(2):76-84 (2008).
Poli, Diana et al., "Exhaled volatile compounds in patients with non-small cell lung cancer: cross sectional and nested short-term follow-up study" Respir Res 6:71-81 (2005).
Poli, Diana et al., "Breath analysis in non small cell lung cancer patients after surgical tumour resection" Acta Biomed 79(Suppl 1):64-72 (2008).
Poli, Diana et al., "Determination of aldehydes in exhaled breath of patients with lung cancer by means of on-fiber-derivatisation SPME—GC/MS" J Chromatograpy B 878(27):2643-2651 (2010).
Rock, Frank et al., "Electronic nose: current status and future trends" Chem Rev 108(2):705-725 (2008).
Shuster, Gregory et al., "Classification of breast cancer precursors through exhaled breath" Breast Cancer Res Treat 126(3):791-796 (2011).
Song, Geng et al., "Quantitative breath analysis of volatile organic compounds of lung cancer patients" Lung Cancer 67(2):227-231 (2010).
Tisch et al. "Nanomaterials for cross-reactive sensor arrays" MRS Bulletin 35(10):797-803 (2010).
Tisch, et al. "Arrays of chemisensitive monolayer-capped metallic nanoparticles for diagnostic breath testing" Rev Chem Eng 26:171-179 (2010).
Wehinger, Andreas et al., "Lung cancer detection by proton transfer reaction mass-spectrometric analysis of human breath gas" Int J Mass Spectrom 265(1):49-59 (2007).
Yu, Hao et al., "Detection volatile organic compounds in breath as markers of lung cancer using a novel electronic nose" Sensors, Proceedings of IEEE 2:1333-1337 (2003).
Zhao, Xiao-Mei et al., "Soft lithographic methods for nano-fabrication" J. Mater. Chem. 7(7):1069-1074 (1997).
Zilberman, Yael et al., "Spongelike Structures of Hexa-peri-hexabenzocoronene Derivatives Enhance the Sensitivity of Chemiresistive Carbon Nanotubes to Nonpolar Volatile Organic Compounds of Cancer" Langmuir 25 (9):5411-5416 (2009).
Zilberman, Yael et al., "Nanoarray of polycyclic aromatic hydrocarbons and carbon nanotubes for accurate and predictive detection in real-world environmental humidity" ACS Nano 5(8):6743-6753 (2011).
American Thoracic Society and European Respiratory Society, "ATS/ERS recommendations for standardized procedures for the online and offline measurement of exhaled lower respiratory nitric oxide and nasal nitric oxide" 2005. Am J Respir Crit Care Med 171(8):912-930 (2005).
The National Lung Screening Trial Research Team "Reduced lung-cancer mortality with low-dose computed tomographic screening" N. Engl J Med 365(5):395-409 (2011).
Barash et al., (2009) Sniffing the unique "odor print" of non-small-cell lung cancer with gold nanoparticles. Small 5(22): 2618-24.
Buszewski et al., (2007) Human exhaled air analytics: biomarkers of diseases. Biomed Chromatogr 2(6): 553-566.
Chan et al., (2009) Elevated levels of oxidative stress markers in exhaled breath condensate. Journal of Thoracic Oncology 4(2): 172-178.
Coate et al., (2009) Molecular predictive and prognostic markers in non-small-cell lung cancer. Lancet Oncol 10(10): 1001-1010.
Coelho et al., (2007) Breath air analysis and its use as a biomarker in biological monitoring of occupational and environmental exposure to chemical agents. J Chromatography B 853(1-2): 1-9.
Coggiola et al., (2004) Volatile organic biomarkers in exhaled breath as a rapid prodromal, diagnosis of bioagent infection. SRI International, Menlo Park CA. 8 pages.
Dovgolevsky et al., (2009) Chemically sensitive resistors based on monolayer-capped cubic nanoparticles: towards configurable nanoporous sensors. Small 5(10): 1158-1161.
Gautschi et al., (2004) Circulating deoxyribonucleic acid as prognostic marker in non-small cell lung cancer patients undergoing chemotherapy. J Clin Oncol 22(20): 4157-4164.
He et al., (2001) Gas Chromatographic-Mass Spectrometric Analysis for Volatile Organic Compound of Human Metabolites in Sealed Cabin. Fenxi Huaxue 29(8): 978-982. Abstract.

(56) References Cited

OTHER PUBLICATIONS

Herth et al., (2009) Narrow-band imaging bronchoscopy increases the specificity of bronchoscopic early lung cancer detection. J Thorac Oncol 4(9): 1060-1065.

Jemal et al., (2009) Cancer statistics, 2009. CA Cancer J Clin 59(4): 225-249.

Matsumura et al., (2009) Urinary volatile compound as biomarkers for lung cancer: A proof of principle study using odor signatures in mouse models of lung cancer. PLos ONE 5(1): 1-11.

Peled et al., (2009) Predictive and prognostic markers for epidermal growth factor receptor inhibitor therapy in non-small cell lung cancer. Ther Adv Med Oncol 1(3): 137-144.

Peled et al., (2012) Detection of volatile organic compounds in cattle naturally infected with *Mycobacterium bovis*. Sensors and Actuators B: Chemical 171-172: 588-594.

Peled et al., (2013) Volatile fingerprints of cancer specific genetic mutations. Nanomedicine 9(6): 758-66.

Phillips et al., (1999) Variation in volatile organic compounds in the breath of normal humans. J Chromatogr B Biomed Sci Appl 729(1-2): 75-88.

Phillips et al., (2003) Volatile markers of breast cancer in the breath. Breast J 9(3): 184-191.

Phillips et al., (2006) Prediction of breast cancer using volatile biomarkers in the breath. Breast Cancer Res Treat 99 (1): 19-21.

Schmutzhard et al., (2008) Pilot study: volatile organic compounds as a diagnostic marker for head and neck tumors. Head Neck 30(6): 743-749.

Sponring et al., (2009) Release of volatile organic compounds from the lung cancer cell line NCI-H2087 in vitro. Anticancer Res 29(1) 419-426.

Witschi et al., (1989) Metabolism and pulmonary toxicity of butylated hydroxytoluene (BHT). Pharmacol Ther 42(1): 89-113.

Xu (2009) The Role of Maintenance Therapy and Biomarkers in Frontline Therapy for Advanced Non-Small-Cell Lung Cancer. A Summary of Selected Presentations From the 45th Annual Meeting of the American Society of Clinical Oncology, May 29-Jun. 2, 2009; Orlando, FL; 4 pages.

Zimmermann et al., (2007) Determination of volatile products of human colon cell line metabolism by GC/MS analysis. Metabolomics 3(1): 13-17.

Sheba Medical Center; Exhaled Breath Biomarkers in Lung Cancer. In: ClinicalTrials.gov. Bethesda (MD): National Library of Medicine (US). Updated Jun. 29, 2011; available from: https://clinicaltrials.gov/ct2/show/NCT01386203 NLM Identifier: NCT01386203; 5 pages.

\* cited by examiner

BREATH ANALYSIS OF PULMONARY NODULES

FIELD OF THE INVENTION

The present invention is directed to a unique profile of volatile organic compounds as breath biomarkers for lung cancer. The present invention is further directed to a system and methods for diagnosis, prognosis and monitoring of lung cancer and predicting the response to certain therapies using non-invasive breath analysis.

BACKGROUND OF THE INVENTION

Lung cancer (LC) is the leading cause of cancer mortality with more than 1 million deaths worldwide every year. The recent National Lung Cancer Screening Trial (NLST) has proven that screening for lung cancer by low dose CT scans reduces the related mortality rate by 20%. Unfortunately, the false-positive rate was extremely high, with 96% of the 24% positive CT findings being non-cancerous. Retrospectively, individuals with false-positive findings underwent unnecessary invasive procedures that are costly and are associated with significant risks and increased mortality (N. Engl. J. Med. 2011; 365:395-409). Since low dose CT screening programs for lung cancer are expected to be launched in many countries in the near future, it is reasonable to expect a dramatic increase in the detection of small solitary pulmonary nodules (SPNs) as well as a dramatic increase in the invasive procedures, morbidity, mortality and health care costs.

Volatile Organic Compounds (VOCs) are organic molecules characterized by a high vapor pressure at ordinary, room temperature conditions. These molecules evaporate from the cell and/or from the surrounding microenvironment and enter the blood stream. Some VOCs are then secreted in exhaled breath through exchange via the lungs. VOCs that evaporate from the membrane of cancer cells induce changes in the blood chemistry. These changes are then reflected in the composition of VOCs in exhaled breath which can be used to diagnose cancer (Expert Rev. Mol. Diagn. 2011; 11: 207-217; memo 2010; 3: 106-112; J. Chromatog. B 2010; 878: 2643-2651; Lung Cancer 2010; 67: 227-231; Br. J. Cancer 2010; 103: 542-551; Nature Nanotech. 2009; 4: 669-673; BMC Cancer 2009; 9: 348; Clin. Chem. 1985; 31: 1278-1282; and Clin. Chem. Lab Med. 2009; 47: 550-560).

In recent years many attempts have been made to identify the breath VOC profile of lung cancer patients (Lancet 1999; 353: 1930-1933; Chest 2003; 123: 2115-2123; Cancer Biomark. 2007; 3: 95-109; Clinica Chimica Acta 2008; 393: 76-84; Lung Cancer 2009; 67: 227-231; Clin. Chem. 1988; 34(8): 1613-1617; Inter. J. Mass Spectro. 2007; 265: 49-59; J. Chromatography A 2009; 1216: 2749-2756; Resp. Res. 2005; 6: 71-81; and Acta Biomed. 2008; 79(1): 64-72). Several spectrometry and spectroscopy studies have shown that the (exhaled breath) VOC profile of patients with lung cancer differs from that of healthy controls without lung nodules (Expert Rev. Mol. Diagn. 2011; 11: 207-217; and memo 2010; 3: 106-112). WO 2010/079491 to one of the inventors of the present invention discloses a set of volatile organic compounds indicative of lung cancer, and methods of diagnosing or monitoring lung cancer progression using such set of volatile organic compounds.

In several cases, matrices of chemical sensors were able to differentiate between breath VOC profiles of patients with lung cancer and healthy controls (Br. J. Cancer 2010; 103: 542-551; Nature Nanotech. 2009; 4: 669-673; Nano Lett. 2008; 8: 3631-3635; Lung Cancer 2009; 64: 166-170; Thorax 2007; 62: 565-568; Amer. J. Resp. Crit. Care Med. 2005; 171: 1286-1291; Sensors, Proceedings of IEEE 2003; 2: 1333-1337; Meas. Sci. Technol. 2005; 16: 1535-1546; and Biosensors and Bioelectronics 2003; 18: 1209-1218).

WO 2007/086986 discloses a method for detecting a target analyte/biomarker in exhaled breath comprising: a) exposing to the exhaled breath a molecular recognition agent capable of selectively binding to the target analyte/biomarker, wherein the molecular recognition agent is linked with a signaling agent; and b) detecting a signal generated by the signaling agent.

WO 2009/066293 to one of the inventors of the present invention discloses an apparatus comprising at least one chemically sensitive sensor for detecting volatile and non-volatile compounds, wherein the chemically sensitive sensor comprises cubic nanoparticle conductive cores capped with an organic coating.

WO 2010/079490 to one of the inventors of the present invention discloses a breath analyzer comprising an array of sensors of conductive nanoparticles capped with an organic coating for detecting cancer.

WO 2009/144725 to one of the inventors of the present invention discloses sensor apparatuses comprising single-walled carbon nanotubes for measuring volatile organic compounds and methods of use thereof for determining breath analytes indicative of various cancers and, in particular, lung cancer.

WO 2010/064239 to one of the inventors of the present application discloses a system comprising an array of sensors for measuring volatile organic compounds as biomarkers for diagnosis, prognosis and monitoring of renal insufficiencies.

In addition to the many studies that were aimed at identifying VOCs indicative of lung cancer from breath samples, Filipiak et al. (Cancer Cell Inter. 2008; 8: 17) disclosed a list of 60 substances observed in the headspace of medium as well as in the headspace of lung cancer cell line CALU-1. A significant increase in the concentrations of 4 VOCs and a decrease in the concentrations of 11 VOCs as compared to medium controls were detected after 18 hours. In another study, Chen et al. (Cancer 2007; 110: 835-844) identified 4 VOCs that were found to exist in all culture mediums of lung cancer cells and can be used as markers of lung cancer. Recent in vitro experiments of the headspace of cell lines identified three substances (decanal, acetophenone and 1,3-bis(1,1-dimethylethyl)-benzene) as main contributors to the separation between small cell and non-small cell lung cancer. Nine VOCs (two aldehydes, one alkane, two ketones, one alcohol and three benzene derivatives) showed differences between subtypes of non-small cell lung cancer of which 2-ethyl-l-hexanol, 1,3-dimethyl-benzene and 1,3-bis (1,1- dimethylethyl)-benzene were found at higher concentrations in the headspace of adenocarcinoma cell lines as compared to the headspace of squamous cell carcinoma cell lines (Nanomedicine (NBM) 2012; 8: 580-589).

WO 2012/023138 to the inventors of the present invention discloses methods of diagnosing, prognosing or monitoring the treatment of pre-cancerous conditions of the lung e.g. bronchial dysplasia or atypical alveolar hyperplasia (AAH), or identifying a genetic alteration which is associated with lung cancer as a means of prognosing or monitoring the treatment or the recurrence of lung cancer, or predicting a patient's response and/or resistance to various treatment regimens.

There remains an unmet need for a reliable biomarker assay technique for differentiating between benign nodules and malignant nodules in a non-invasive and cost-effective manner while dramatically reducing false-positive rates.

SUMMARY OF THE INVENTION

The present invention provides the use of 1-octene as a unique breath biomarker for lung cancer. The present invention further provides a system and methods for diagnosing, monitoring or prognosing lung cancer or differentiating between benign and malignant solitary pulmonary nodules, small cell and non-small cell lung cancer, adenocarcinoma and squamous cell carcinoma, and early and advanced stage lung cancer. The system and methods of the present invention can be used for predicting the responses to anti-cancer therapy (classical chemotherapy and/or targeted therapy).

The present invention is based in part on the unexpected finding of a unique profile of
VOCs for diagnosing lung cancer and the identification of 1-octene as a novel breath biomarker for lung cancer. Surprisingly, the use of a sensor array comprising at least one sensor comprising a random network of carbon nanotubes coated with polycyclic aromatic hydrocarbons and at least one sensor comprising film/assembly of metal nanoparticles coated with an organic coating, preferably thiols, in conjunction with a pattern recognition algorithm afforded the differentiation between benign and malignant solitary pulmonary nodules, small cell and non-small cell lung cancer, adenocarcinoma and squamous cell carcinoma, and early and advanced stage lung cancer.

According to a first aspect, the present invention provides a set of volatile organic compounds as breath biomarkers for lung cancer, wherein the set comprises 1-octene.

According to another aspect, the present invention provides a method of diagnosing, monitoring or prognosing lung cancer in a subject or predicting a patient's response to a treatment regimen, the method comprising the steps of: a) collecting a test breath sample from a test subject; b) determining the level of at least one volatile organic compound from a set of volatile organic compounds in the test sample, wherein the set of volatile organic compounds comprises 1-octene; and c) comparing the level of the at least one volatile organic compound from the test sample with the level of said at least one volatile organic compound in a control sample, whereby a significantly different level of said at least one volatile organic compound in the test sample as compared to the level of said compound in the control sample is indicative of lung cancer or provides the prediction of a patient's response to a treatment regimen.

In one embodiment, the level of the at least one volatile organic compound in the test sample is increased as compared with the level of said compound in the control sample.

In another embodiment, the level of the at least one volatile organic compound in the test sample is decreased as compared with the level of said compound in the control sample.

In particular embodiments, the levels of a plurality of volatile organic compounds in the breath sample from a lung cancer patient form a pattern which is significantly different from the pattern of said volatile organic compounds in the control sample. According to further embodiments, the pattern is significantly different from a predetermined pattern of occurrence of volatile organic compounds in breath samples.

According to various embodiments, the control sample may be obtained from a reference group comprising subjects that are not afflicted with lung cancer (negative control). In alternative embodiments, the control sample may be obtained from a population of patients known to be afflicted with lung cancer (positive control). The control sample, according to the principles of the present invention is obtained from at least one subject, preferably a plurality of subjects. A set of control samples may be stored as a reference collection of data.

According to some embodiments, the step of determining the levels of volatile organic compounds in a sample comprises the use of at least one technique selected from the group consisting of Gas-Chromatography (GC), GC-lined Mass-Spectrometry (GC-MS), Proton Transfer Reaction Mass-Spectrometry (PTR-MS), Electronic nose device, and Quartz Crystal Microbalance (QCM). Each possibility represents a separate embodiment of the present invention.

In a particular embodiment, the step of determining the levels of volatile organic compounds in a sample further comprises the use of a breath concentrator.

In an exemplary embodiment, the step of determining the levels of volatile organic compounds in a sample comprises the use of Gas-Chromatography-Mass Spectrometry (GC-MS) combined with solid phase microextraction (SPME).

In specific embodiments, solid phase microextraction comprises the use of extraction fibers coated with at least one polymer selected from the group consisting of divinylbenzene, carboxen, polydimethylsiloxane and combinations thereof. Each possibility represents a separate embodiment of the present invention.

In various embodiments, the test subject is selected from a subject who is at risk of developing lung cancer, a subject who is suspected of having lung cancer, and a subject who is afflicted with lung cancer. Each possibility represents a separate embodiment of the present invention.

According to yet another aspect, the present invention provides a system for diagnosing, monitoring or prognosing lung cancer or stages or subtypes thereof in a subject or predicting a patient's response to a treatment regimen, the system comprising: (a) an apparatus comprising at least one sensor comprising single walled carbon nanotubes coated with polycyclic aromatic hydrocarbons, and at least one sensor comprising metal nanoparticles coated with an organic coating; (b) a detection means; and (c) a processing unit comprising a pattern recognition analyzer, wherein the pattern recognition analyzer receives sensor output signals and compares them to stored data so as to enable the diagnosis, monitoring or prognosis of lung cancer or stages or subtypes thereof or the prediction of a patient's response to a treatment regimen.

In some embodiments, the polycyclic aromatic hydrocarbons are selected from arenes, polyarenes, and combinations thereof. Each possibility represents a separate embodiment of the present invention. In certain embodiments, the arenes or polyarenes are selected from the group consisting of naphthalene, acenaphtene, anthracene, phenanthrene, pyrene, benzo[a]pyrene, chrysene, fluoranthene, $C_{18}$-$C_{180}$ graphenes and combinations thereof. Each possibility represents a separate embodiment of the present invention. In specific embodiments, the arenes or polyarenes are $C_{18}$-$C_{180}$ graphenes, for example $C_{42}$ graphene, $C_{50}$ graphene and the like.

In various embodiments, the arenes or polyarenes are substituted with hydrophobic or hydrophilic carbon chains and/or at least one functional group selected from the group consisting of ester, ether, alcohol, amine, imine, amide, ammonium, keto, aldehyde, halogen (halo), pyridyl, phosphate, thiol, sulfonate, sulfonyl, hydroxyl, carboxylate, carboxyl, and carbonate groups. Each possibility represents a separate embodiment of the present invention.

In particular embodiments, the polycyclic aromatic hydrocarbons comprise hexa-peri-hexabenzocoronene (HBC) molecules, which are unsubstituted or substituted by any one of 2-ethyl-hexyl (HBC-$C_{6,2}$), 2-hexyldecane (HBC-$C_{10,6}$), 2-decyl tetradecane (HBC-$C_{14,10}$), and dodecane (HBC-$C_{12}$). Each possibility represents a separate embodiment of the present invention.

In another embodiment, the single walled carbon nanotubes are organized in a random network configuration. In other embodiments, the single walled carbon nanotubes have diameters ranging from about 0.9 nanometer to about 5 nanometers, and lengths ranging from about 1 micrometer to about 50 micrometers.

In further embodiments, the metal nanoparticles are selected from the group consisting of Au, Ag, Ni, Co, Pt, Pd, Cu, and Al nanoparticles and combinations thereof Each possibility represents a separate embodiment of the present invention. In an exemplary embodiment, the metal nanoparticles are gold (Au) nanoparticles.

In some embodiments, the organic coating of the metal nanoparticles comprises compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof. Each possibility represents a separate embodiment of the present invention.

In certain embodiments, the organic coating of the metal nanoparticles comprises thiols.

In particular embodiments, the organic coating of the metal nanoparticles comprises compounds selected from the group consisting of hexanethiol, 2-ethylhexanethiol, 3-methyl-1-butanethiol, octadecylamine, decanethiol, dodecanethiol, 2-mercaptobenzoazole, 4-methoxy-toluenethiol, tert-dodecanethiol, 2-amino-4-chlorobenzenethiol, 2-mercaptobenzimidazole, benzylmercaptan, 2-nitro-4-trifluoromethylbenzenethiol, 2-naphthalenethiol, 2-nitro-4-trifluoromethylbenzenethiol, and combinations thereof. Each possibility represents a separate embodiment of the present invention.

In other embodiments, the metal nanoparticles have a morphology selected from a cubic, a spherical, and a spheroidal morphology. Each possibility represents a separate embodiment of the present invention.

In certain embodiments, the at least one sensor is configured in a form selected from the group consisting of a capacitive sensor, a resistive sensor, a chemoresistive sensor, an impedance sensor, and a field effect transistor sensor. Each possibility represents a separate embodiment of the present invention.

In some embodiments, the system comprises between 2 and 20 sensors, for example 8 sensors, 13 sensors, 18 sensors and the like. In other embodiments, the detection means comprises a device for measuring changes in resistance, conductance, alternating current (AC), frequency, capacitance, impedance, inductance, mobility, electrical potential, optical property or voltage threshold. Each possibility represents a separate embodiment of the present invention.

In a further aspect, the present invention provides a method of diagnosing, monitoring or prognosing lung cancer or stages or subtypes thereof in a subject or predicting a patient's response to a treatment regimen, the method comprising the steps of: (a) providing a system comprising an apparatus comprising at least one sensor comprising single walled carbon nanotubes coated with polycyclic aromatic hydrocarbons, and at least one sensor comprising metal nanoparticles coated with an organic coating; a detection means; and a processing unit comprising a pattern recognition analyzer comprising at least one pattern recognition algorithm; (b) exposing the apparatus to a test exhaled breath sample; (c) measuring at least one response induced parameter from the apparatus upon exposure to the test sample to obtain a response pattern; and (d) analyzing the response pattern obtained in step (c) using a pattern recognition algorithm by comparing it to stored data obtained from a control sample whereby a significantly different response pattern of the test sample as compared the control sample is indicative of lung cancer or stages or subtypes thereof or provides the prediction of a patient's response to a treatment regimen.

In some embodiments, the method of diagnosing, monitoring or prognosing lung cancer or stages or subtypes thereof in a subject or predicting a patient's response to a treatment regimen further enables the differentiation between subjects having benign solitary pulmonary nodules and subjects having malignant solitary pulmonary nodules. In other embodiments, the method enables the differentiation between subjects having small cell lung cancer and subjects having non-small cell lung cancer, and further enables the differentiation between subjects having non-small cell lung cancer in an early stage and subjects having non-small cell lung cancer in an advanced stage. In additional embodiments, the method enables the differentiation between subjects having adenocarcinoma and subjects having squamous cell carcinoma. In further embodiments, the method enables the differentiation between subjects having lung cancer and subjects having lung metastases.

In certain embodiments, the method of diagnosing, monitoring or prognosing lung cancer or stages or subtypes thereof in a subject or predicting a patient's response to a treatment regimen is directed to prognosing a subject who is suspected of having lung cancer.

In other embodiments, the method is directed to a subject having malignant solitary pulmonary nodules.

The detected pattern can be analyzed using a pattern recognition analyzer which utilizes at least one pattern recognition algorithm. Suitable pattern recognition algorithms include, but are not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the present invention. In an exemplary embodiment, the algorithm used to analyze the pattern is discriminant factor analysis (DFA).

In certain embodiments, the response pattern is formed by the sensors detection of at least one volatile biomarker which is indicative of lung cancer or stages or subtypes thereof. In particular embodiments, the at least one volatile biomarker which is indicative of lung cancer or stages or subtypes thereof is 1-octene.

In various embodiments, the test subject is a mammal, preferably a human.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
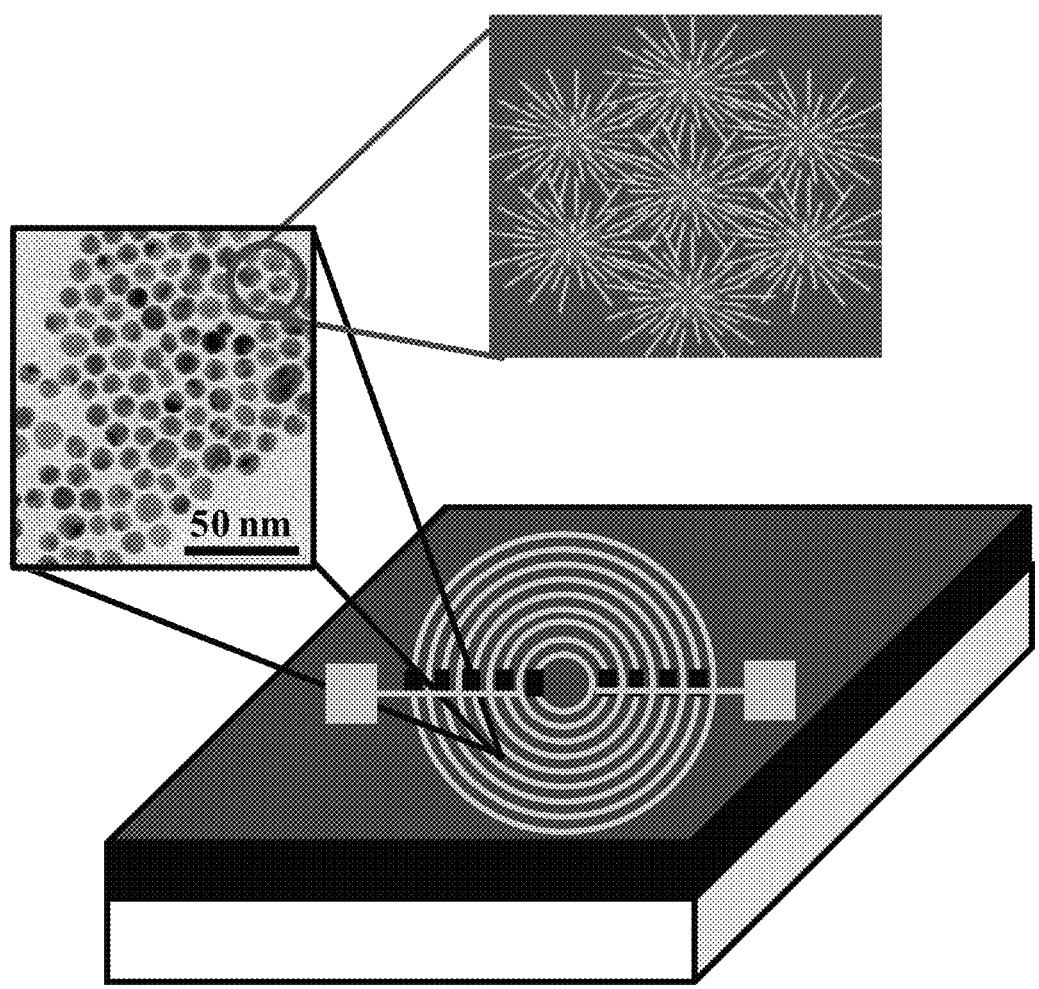
FIG. 1. Schematic representation of the GNP sensors (not drawn to scale). The left inset shows a representative transmission electron micrograph (TEM) of the organically functionalized GNPs in solution.

The present invention provides methods of diagnosis, prognosis and monitoring lung cancer, stages and subtypes thereof or predicting a patient's response to a treatment regimen by detecting a VOC profile which differs from the VOC profile of a control sample thus being indicative for the presence of lung cancer. Detection of the VOC profile is obtained, in some embodiments, using a system comprising at least one sensor comprising carbon nanotubes coated with polycyclic aromatic hydrocarbon molecules and at least one sensor comprising metal nanoparticles capped with an organic coating (e.g. thiols). The methods of the present invention provide the differentiation between benign and malignant solitary pulmonary nodules, small cell and non-small cell lung cancer, adenocarcinoma and squamous cell carcinoma, and early and advanced stage lung cancer and further provide the differentiation between lung cancer and lung metastases.

The methods of the present invention can be utilized for primary and/or secondary screening for malignant solitary pulmonary nodules. The methods may be used for the management of patients with pulmonary nodules (personalized medicine), and may reduce the false positive rate and minimize the risk of morbidity related to invasive diagnostic procedures.

The present inventors have discovered unexpectedly, that 1-octene can be found at elevated levels in exhaled breath of patients having lung cancer. Nowhere in the background art was it taught or suggested that the occurrence of 1-octene in elevated levels in the breath of an individual can be used to diagnose lung cancer or stages or subtypes thereof. The present invention provides methods of breath analysis for determining the presence of lung cancer and further differentiating between patients having small cell and non-small cell lung cancer at various stages, and patients having adenocarcinoma and squamous cell carcinoma.

The present invention thus provides a volatile organic compound (VOC) profile which is indicative of lung cancer in a breath sample. The (VOC) profile is characterized by 1-octene concentration/level which is significantly different than the concentration/level of 1-octene in a negative control sample. The control sample, according to the principles of the present invention, is obtained from an individual who has no lung cancer or any other type of cancer. Preferably, the control sample is obtained from an individual whose lungs are essentially devoid of benign tumors. The term "significantly different" as used herein refers to a quantitative difference in the concentration or level of a VOC as compared to its concentration or level in control samples. A statistically significant difference can be determined by any test known to the person skilled in the art. Common tests for statistical significance include, among others, t-test, ANOVA1 Kruskal-Wallis, Wilcoxon, Mann-Whitney and odds ratio. Individual samples (of unknown status) can be compared with data obtained from the reference group (negative control), and/or compared with data obtained from a positive control group known to have lung cancer. An increase or decrease in the level as compared to a control or reference value or mean control level or reference value, or a change, difference or deviation from a control or reference value, can be considered to exist if the level differs from the control level or reference value, by about 5% or more, by about 10% or more, by about 20% or more, or by about 50% or more compared to the control level or reference value. Statistical significance may alternatively be calculated as $P<0.05$. Methods of determining statistical significance are known and are readily used by a person of skill in the art. In a further alternative, increased levels, decreased levels, deviation, and changes can be determined by recourse to assay reference limits or reference intervals. These can be calculated from intuitive assessment or non- parametric methods. Overall, these methods calculate the 0.025, and 0.975 fractiles as 0.025* (n+1) and 0.975*(n+1). Such methods are well known in the art. The presence of a VOC marker which is absent in a control sample, is also contemplated as an increased level, deviation or change. The absence of a VOC marker which is present in a control, for example, is also contemplated as a decreased level, deviation or change.

According to the principles of the present invention, the set of volatile organic compounds which are indicative of lung cancer comprises VOCs that are present in breath samples of lung cancer patients in levels which are at least one standard deviation [SD] larger or smaller than their mean level in breath samples of a negative control population. More preferably, the levels of VOCs in breath samples of lung cancer patients are at least 2[SD] or 3[SD] larger or smaller than their mean level in breath samples of a negative control population. Accordingly, individual samples (of unknown status) are considered to belong to a sick population when the level of VOCs is at least 1[SD], 2[SD] or 3[SD] larger or smaller than the mean level of VOCs in breath samples of a negative control population.

Alternatively, the set of VOCs is characterized by a pattern which significantly differs from the patterns of said VOCs in control samples, or wherein the pattern is significantly different from a predetermined pattern of occurrence of VOCs.

The present invention further provides a method of diagnosing, monitoring or prognosing lung cancer or stages or subtypes thereof in a subject. The method further provides the prediction of a patient's response to a treatment regimen. The method comprises the collection of a breath sample from a test subject followed by the determination of the level of at least one VOC from a set of VOCs which are indicative for lung cancer. In some embodiments, the at least one VOC whose level is determined is 1-octene. The method then comprises comparing the level of said VOC with the level of said VOC in a control sample, wherein a significantly differing level of said VOC in the test sample as compared to the level of said VOC in the control sample is indicative of lung cancer or provides the prediction of a patient's response to a treatment regimen.

The collection of a breath sample, according to the principles of the present invention, can be performed in any manner known to a person of ordinary skill in the art. In exemplary embodiments, the breath sample may be collected using a breath collector apparatus. Specifically, the breath collector apparatus is designed to collect alveolar breath samples. Exemplary breath collector apparatuses within the scope of the present invention include apparatuses approved by the American Thoracic Society/European Respiratory Society (ATS/ERS); Am. J. Respir. Crit. Care Med. 2005; 171: 912). Alveolar breath is usually collected from individuals using the off-line method.

In certain embodiments, the sample is pre-concentrated prior to the measurement of VOCs. Breath concentrators that are within the scope of the present invention include, but are not limited to, I. Solid Phase Microextraction (SPME)—The SPME technique is based on a fiber coated with a liquid (polymer), a solid (sorbent), or combination thereof. The fiber coating extracts the compounds from the sample either by absorption (where the coating is liquid) or by adsorption (where the coating is solid). Non-limiting examples of coating polymers include divinylbenzene, carboxen, polydimethylsiloxane and combinations thereof.

II. Sorbent Tubes—Sorbent tubes are typically composed of glass and contain various types of solid adsorbent material (sorbents). Commonly used sorbents include activated charcoal, silica gel, and organic porous polymers such as Tenax and Amberlite XAD resins. Sorbent tubes are attached to air sampling pumps for sample collection. A pump with a calibrated flow rate in ml/min draws a predetermined volume of air through the sorbent tube. Compounds are trapped onto the sorbent material throughout the sampling period. This technique was developed by the U.S. National Institute for Occupational Safety and Health (NIOSH).

III. Cryogenic Concentrations—Cryogenic condensation is a process that allows recovery of volatile organic compounds (VOCs) for reuse. The condensation process requires very low temperatures so that VOCs can be condensed. Traditionally, chlorofluorocarbon (CFC) refrigerants have been used to condense the VOCs. Currently, liquid nitrogen is used in the cryogenic (less than $-160\,°$ C.) condensation process.

The determination of the level of at least one volatile organic compounds is performed, according to the principles of the present invention, by the use of at least one technique including, but not limited to, Gas-Chromatography (GC), GC-lined Mass-Spectrometry (GC-MS), Proton Transfer Reaction Mass-Spectrometry (PTR-MS), Electronic nose device (E-nose), and Quartz Crystal Microbalance (QCM). Each possibility represents a separate embodiment of the present invention.

Gas Chromatography (GC) linked to mass spectrometry (MS) is often used to determine the chemical identity and composition of breath VOCs (Clinica Chimica Acta 2004; 347: 25-39). In this set-up, the GC utilizes a capillary column having characteristic dimensions (length, diameter, film thickness) as well as characteristic phase properties. The difference in the chemical properties of different molecules in a mixture allows the separation of the molecules as the sample travels through the column, wherein each molecule has a characteristic time (termed retention time) in which it passes through the column under set conditions. This allows the mass spectrometer to capture, ionize, accelerate, deflect, and detect the ionized molecules separately. The MS signal is obtained by ionization of the molecules or molecular fragments and measurement of their mass to charge ratio by comparing it to a reference collection.

Proton transfer reaction-mass spectrometry (PTR-MS) is reviewed in Int. J. Mass Spectrom. Ion Process 1998; 173: 191-241; and Adv. Gas Phase Ion Chem. 2001; 4: 1-35.

Briefly, PTR-MS measures VOCs that react with $H_3O^+$ ions that are added from an ion source. VOCs with a proton affinity that is larger than that of water (166.5 kcal×mol$^{-1}$) undergo a proton-transfer reaction with the $H_3O^+$ ions as follows: $H_3O^+ + R \rightarrow RH^+ + H_2O$. At the end of the drift tube reactor, a fraction of the ions is sampled by a quadrupole mass spectrometer, which measures the $H_3O^+$ and $RH^+$ ions. The ion signal at a certain mass is linearly dependent on the concentration of the precursor VOC in the sample. In PTR-MS only the mass of VOCs is determined, causing some ambiguity in the identity of the VOCs. Thus, this technique does not allow a separate detection of different VOCs having the same mass. Further overlap of ion masses is caused by a limited degree of ion fragmentation and ion clustering in the drift tube.

Quartz Crystal Microbalance (QCM) is a piezoelectric-based device which can measure very small mass changes, mostly down to few nanograms. Briefly, QCM works by sending an electrical signal through a gold-plated quartz crystal, which causes vibrations in the crystal at a specific resonant frequency measured by the QCM. The resulted frequency shift can be translated to a change in mass on the QCM surface, mostly via using the Sauerbrey equation:

$$\Delta f = \frac{-2f_0^2}{A\sqrt{\rho_q \mu_q}} m$$

This equitation is used to correlate changes in the oscillation frequency of a piezoelectric crystal ($\Delta f$) with the mass deposited on it ($\Delta m$). Other parameters which affect the signals are the resonant frequency ($f_0$), the area between electrodes of the piezo-electric crystal (A), density ($\rho_q$) and the shear modulus ($\mu_q$) of quartz.

Electronic nose devices perform odor detection through the use of an array of broadly cross-reactive sensors in conjunction with pattern recognition methods (Chem. Rev. 2008; 108: 705-725). In contrast to the "lock-and-key" approach, each sensor in the electronic nose device is broadly responsive to a variety of odorants. In this architecture, each analyte produces a distinct fingerprint from the array of broadly cross-reactive sensors.

This allows to considerably widen the variety of compounds to which a given matrix is sensitive, to increase the degree of component identification and, in specific cases, to perform an analysis of individual components in complex multi-component (bio) chemical media. Pattern recognition algorithms can then be used to obtain information on the identity, properties and concentration of the vapor exposed to the electronic nose device.

In some embodiments, the electronic nose device comprises a system which is suitable for the diagnosis, monitoring or prognosis of lung cancer at its various stages via the detection of a unique profile of volatile specific biomarkers in exhaled breath samples. The system may further provide the prediction or assessment of the response to a certain anti-cancer treatment. The system includes at least two chemically sensitive sensors as described herein, a detection means and a processing unit which utilizes at least one pattern recognition algorithm to receive sensor output signals and compare them to stored data so as to enable the diagnosis, monitoring or prognosis of lung cancer or stages or subtypes thereof or the prediction or assessment of the response to a certain treatment.

According to the principles of the present invention, the system comprises a combination of chemically sensitive sensors. Specifically, the system comprises a sensor array comprising at least one sensor comprising single-walled carbon nanotubes (SWCNTs) coated with polycyclic aromatic hydrocarbons and at least one sensor comprising metal nanoparticles coated with an organic coating as defined herein.

In some embodiments, the single-walled carbon nanotubes are arranged in a random network configuration. In other embodiments, the network of SWCNTs can be fabricated by a physical manipulation or in a self-assembly process. The term "self-assembly" as used herein refers to a process of the organization of molecules without intervening from an outside source. The self-assembly process occurs in a solution/solvent or directly on a solid-state substrate.

Main approaches for the synthesis of carbon nanotubes in accordance with the present invention include, but are not limited to, laser ablation of carbon, electric arc discharge of graphite rod, and chemical vapor deposition (CVD) of hydrocarbons. Among these approaches, CVD coupled with photolithography has been found to be the most versatile in the preparation of various carbon nanotube devices. In a CVD method, a transition metal catalyst is deposited on a substrate (e.g. silicon wafer) in the desired pattern, which may be fashioned using photolithography followed by etching. The substrate having the catalyst deposits is then placed in a furnace in the presence of a vapor-phase mixture of, for example, xylene and ferrocene. Carbon nanotubes typically grow on the catalyst deposits in a direction which is normal to the substrate surface. Various carbon nanotube materials and devices are now available from commercial sources.

Other CVD methods include the preparation of carbon nanotubes on silica ($SiO_2$) and silicon surfaces without using a transition metal catalyst. Accordingly, areas of silica are patterned on a silicon wafer by photolithography and etching. Carbon nanotubes are then grown on the silica surfaces in a CVD or a plasma-enhanced CVD (PECVD) process. These methods provide the production of carbon nanotube bundles in various shapes.

The term "single walled carbon nanotube" as used herein refers to a cylindrically shaped thin sheet of carbon atoms having a wall which is essentially composed of a single layer of carbon atoms which are organized in a hexagonal crystalline structure with a graphitic type of bonding. A nanotube is characterized by the length-to-diameter ratio. It is to be understood that the term "nanotubes" as used herein refers to structures in the nanometer as well as in the micrometer range.

According to various embodiments, the single-walled carbon nanotubes of the present invention have diameters ranging from about 0.6 nanometers (nm) to about 100 nm and lengths ranging from about 50 nm to about 10 millimeters (mm). More preferably, the single-walled carbon nanotubes have diameters ranging from about 0.7 nm to about 50 nm and lengths ranging from about 250 nm to about 1 mm. Even more preferably, the single-walled carbon nanotubes have diameters ranging from about 0.8 nm to about 10 nm and lengths ranging from about 0.5 micrometer ($\mu m$) to about 100 $\mu m$. Most preferably, the single-walled carbon nanotubes of the present invention have diameters ranging from about 0.9 nm to about 5 nm and lengths ranging from about 1 $\mu m$ to about 50 $\mu m$.

According to the principles of the present invention, the single walled carbon nanotubes are coated with polycyclic aromatic hydrocarbon molecules. Suitable polycyclic aromatic hydrocarbon molecules include, but are not limited to, arenes, polyarenes and combinations thereof. As used herein the term "arene" refers to single as well as linked or fused aromatic rings which may be further substituted. The term "polyarene" as used herein refers to polycyclic aromatic hydrocarbons which comprise three or more rings, wherein at least two of which are aromatic and in which at least two of these aromatic rings are fused by sharing two adjacent carbon atoms. Suitable arenes or polyarenes include, but are not limited to, naphthalene, acenaphtene, anthracene, phenanthrene, pyrene, benzo[a]pyrene, chrysene, fluoranthene, $C_{18}$-$C_{180}$ graphenes and combinations thereof.

Each possibility represents a separate embodiment of the present invention. The term "arene" further includes heteroarenes wherein one or more ring carbon atoms of the arene is replaced with a heteroatom (e.g., N, S, P or O), for example, phenyl-thiophenyl-phenyl-thiophenyl. Arenes may be non-functionalized (un-substituted) or may be functionalized with one or more substituents, for example hydrophobic or hydrophilic carbon chains. In addition, the arenes or the hydrophoboic or hydrophilic carbon chains may be functionalized with least one functional group including, but not limited to, ester, ether, alcohol, amine, imine, amide, ammonium, keto, aldehyde, halogen (halo), pyridyl, phosphate, thiol, sulfonate, sulfonyl, hydroxyl, carboxylate, carboxyl, and carbonate groups. Each possibility represents a separate embodiment of the present invention.

One class of arenes or polyarenes within the scope of the present invention is $C_{18}$-$C_{180}$ graphenes, for example $C_{42}$ graphene, $C_{50}$ graphene and the like. The term "graphene" as used herein refers to a molecule in which a plurality of carbon atoms (e.g., in the form of five-membered rings, six-membered rings, and/or seven-membered rings) are covalently bound to each other to form a (typically sheet-like) polycyclic aromatic molecule. In one embodiment, the graphene comprises a single layer of carbon atoms that are covalently bound to each other (most typically sp$^2$ bonded). It should be noted that such sheets may have various configurations, and that the particular configuration will depend, inter alia, on the amount and position of five-membered and/or seven-membered rings in the sheet. In another embodiment, the graphene comprises several (e.g., two, three, four, five to ten, one to twenty, one to fifty, or one to hundred) single layers of carbon atoms which are stacked together to a maximum thickness of less than about 100 nanometers.

In one embodiment, the polycyclic aromatic hydrocarbon molecules are functionalized with a carbon chain which comprises at least one ether group (e.g. ether (methyl) group, ether (ethyl) group and the like). In various embodiments, the polycyclic aromatic hydrocarbon molecules comprise hexa-peri-hexabenzocoronene (HBC) molecules, which are unsubstituted or substituted by any one of 2-ethyl-hexyl (HBC-$C_{6,2}$), 2-hexyldecane (HBC-$C_{10,6}$), 2-decyl tetradecane (HBC-$C_{14,10}$), and dodecane (HBC-$C_{12}$). Each possibility represents a separate embodiment of the present invention.

The system of the present invention comprises at least one sensor comprising metal nanoparticles which are coated with an organic coating. Suitable non-limiting examples of metal nanoparticles include, but are not limited to, Au, Ag, Ni, Co, Pt, Pd, Cu, and Al nanoparticles and combinations thereof. Each possibility represents a separate embodiment of the present invention.

Suitable coating of the metal nanoparticles includes, but not limited to, alkylthiols, e.g., alkylthiols with $C_3$-$C_{24}$ chains, arylthiols, alkylarylthiols, alkenyl thiols, alkynyl thiols, cycloalkyl thiols, heterocyclyl thiols, heteroaryl thiols, alkylthiolates, alkenyl thiolates, alkynyl thiolates, cycloalkyl thiolates, heterocyclyl thiolates, heteroaryl thiolates, ω-functionalized alkanethiolates, arenethiolates, (γ-mercaptopropyl)tri-methyloxysilane, dialkyl disulfides and combinations thereof. Each possibility represents a separate embodiment of the present invention. In particular embodiments, the metal nanoparticles are coated with thiols.

Exemplary coating of the metal nanoparticles includes, but is not limited to, hexanethiol, 2-ethylhexanethiol, 3-methyl-1-butanethiol, octadecylamine, decanethiol, dodecanethiol, 2-mercaptobenzoazole, 4-methoxy-toluenethiol, tert-dodecanethiol, 2-amino-4-chlorobenzenethiol, 2-mercaptobenzimidazole, benzylmercaptan, 2-nitro-4-trifluoromethylbenzenethiol, 2-naphthalenethiol, 2-nitro-4-trifluoromethylbenzenethiol, and combinations thereof. Each possibility represents a separate embodiment of the present invention.

Sensors comprising organically functionalized metal nanoparticles can be synthesized as is known in the art, for example using the two-phase method (J. Chem. Soc. Chem. Commun. 1994; 7: 801-802) with some modifications (Langmuir 1998; 14(1): 17-30). Organically functionalized gold nanoparticles can be synthesized by transferring AuCl$_4^-$ from aqueous HAuCl$_4$·xH$_2$O solution to a toluene solution by the phase-transfer reagent TOAB.

After isolating the organic phase, excess thiols are added to the solution. The mole ratio of thiol: HAuCl$_4$·xH$_2$O can vary between 1:1 and 10:1, depending on the thiol used. This is performed in order to prepare mono-disperse solution of gold nanoparticles in an average size of about 3.5-5 nm. Exemplary procedures include, but are not limited to, thiol: Au mole ratios of 10:1 and 1:1 for dodecanethiol and butanethiol-capped gold nanoparticles, respectively at an average size of about 5 nm. After vigorous stirring of the solution, aqueous solution of the reducing agent NaBH$_4$ in large excess is added. The reaction is constantly stirred at room temperature for at least 3 hours to produce a dark brown solution of the thiol-capped Au nanoparticles. The resulting solution is further subjected to solvent removal in a rotary evaporator followed by multiple washings using ethanol and toluene. Gold nanoparticles capped with 2-mercaptobenzimidazole can be synthesized by the ligand-exchange method from pre-prepared hexanethiol-capped gold nanoparticles. In a typical reaction, excess of thiol, 2-mercaptobenzimidazole, is added to a solution of hexanethiol-capped gold nanoparticles in toluene. The solution is kept under constant stirring for a few days in order to allow as much ligand conversion as possible. The nanoparticles are purified from free thiol ligands by repeated extractions. The metal nanoparticles may have any desirable morphology including, but not limited to, a cubic, a spherical, and a spheroidal morphology. Each possibility represents a separate embodiment of the present invention.

The synthesized organically functionalized metal nanoparticles can then be assembled (e.g. by a self-assembly process) to produce a film. The term "film", as used herein, corresponds to a configuration of well-arranged assembly of organically functionalized metal nanoparticles. 2D films or 3D film assemblies (stacked films) may also be used. Exemplary methods for obtaining well-ordered two or three dimensional films/assemblies of organically functionalized metal nanoparticles include, but are not limited to, i. Random deposition from solution of organically functionalized nanoparticles on solid surfaces. The deposition is performed by drop casting, spin coating, spray coating and other similar techniques.

ii. Field-enhanced or molecular-interaction-induced deposition from solution of organically functionalized nanoparticles on solid surfaces.

iii. Langmuir-Blodgett or Langmuir-Schaefer techniques. The substrate is vertically plunged through self-organized/well-ordered 2D monolayer of organically functionalized nanoparticles at the air-subphase interface, wherein the latter is being subsequently transferred onto it. Multiple plunging of the substrate through the 2D monolayer of organically functionalized nanoparticles at the air-subphase interface, results in the fabrication of the 3D-ordered multilayers of organically functionalized nanoparticles.

iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating organically functionalized nanoparticles from nanometer-scale to a mesoscopic scale (J. Mater. Chem. 1997; 7(7): 1069-1074).

v. Various combinations of Langmuir-Blodgett or Langmuir-Schaefer methods with soft lithographic techniques can be used to produce patterned Langmuir-Blodgett films of organically functionalized nanoparticles which are transferred onto solid substrates.

vi. Printing on solid-state or flexible substrates using an inject printer designated for printed electronics. A solution containing organically functionalized nanoparticles is used as a filling material (or "ink") of the printing head according to procedures well known in the art.

The sensors of the present invention can be configured as any one of the various types of electronic devices, including, but not limited to, capacitive sensors, resistive sensors, chemiresistive sensors, impedance sensors, field effect transistor sensors, and the like, or combinations thereof. Each possibility represents a separate embodiment of the present invention.

The system of the present invention comprises a plurality of sensors (sensor array), for example between 2 and 20 sensors (i.e. 8 sensors, 13 sensors, 18 sensors and the like). In certain embodiments, the sensors of the present invention comprise one or more conducting elements. The conducting elements may include a source and a drain electrode separated from one another by a source-drain gap.

The system disclosed herein may further comprise a gate electrode wherein the sensor signal may be indicative of a certain property of the nanomaterial under the influence of a gate voltage. In some embodiments, the sensor signal may be indicative of a capacitance property of the nanomaterial.

The sensor signal may be induced, according to the principles of the present invention by a change in any one or more of conductivity, resistance, impedance, capacitance, inductance, or optical properties of the sensors upon exposure to volatile biomarkers. Changes in the optical properties of the sensor(s) can be measured using e.g., spectroscopic ellipsometry.

The sensor signal is detected by a detection means. Suitable detection means include devices which are susceptible to a change in any one or more of resistance, conductance, alternating current (AC), frequency, capacitance, impedance, inductance, mobility, electrical potential, optical property and voltage threshold. Each possibility represents a separate embodiment of the present invention. In additional embodiments, the detection means includes devices which are susceptible to swelling or aggregation of nanomaterials as well as devices which are susceptible to a change in any one or more of optical signal, florescence, chemiluminsence, photophorescence, bending, surface acoustic wave, piezoelectricity and the like. Each possibility represents a separate embodiment of the present invention.

In some embodiments, the sensing signal is obtained through the adsorption of the analyte/volatile biomarker on the nanomaterial. According to the principles of the present invention, the signal is generated by the change in conformation/structure of the nanomaterial upon analyte/volatile biomarker adsorption. The present invention thus provides the direct sensing of the analyte/volatile biomarker thereby obviating the need for a signaling agent.

According to another embodiment, the present invention further provides a processing unit comprising a pattern recognition analyzer, wherein the pattern recognition analyzer receives sensor output signals and analyzes them by at least one pattern recognition algorithm to produce an output signature. By comparing an unknown signature with a database of stored or known signatures, volatile biomarkers can be identified. The analyzer utilizes pattern recognition algorithms comprising artificial neural networks, such as multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods such as principal component analysis (PCA), partial least squares (PLS), multiple linear regression (MLR), principal component regression (PCR), discriminant function analysis (DFA) including linear discriminant analysis (LDA), and cluster analysis including nearest neighbor. Each possibility represents a separate embodiment of the present invention. In an exemplary embodiment, the algorithm used for processing the data is discriminant function analysis (DFA).

Additional algorithms suitable for identifying patterns of volatile biomarkers and quantifying their concentration include, but are not limited to, Fisher linear discriminant analysis (FLDA), soft independent modeling of class analogy (SIMCA), K-nearest neighbors (KNN), neural networks, genetic algorithms, and fuzzy logic algorithms. Each possibility represents a separate embodiment of the present invention. In some embodiments, the Fisher linear discriminant analysis (FLDA) and canonical discriminant analysis (CDA) and combinations thereof are used to compare the output signature and the available data from the database. Other classification techniques may also be employed. After analysis is completed, the resulting information can be displayed on a display or transmitted to a host computer.

The present invention further provides a method of diagnosing, monitoring or prognosing lung cancer or stages or subtypes thereof in a subject or predicting the response to certain therapies using the system of the present invention. The sensor array is exposed to a test exhaled breath sample and at least one response induced parameter is measured by a detection means. The obtained signal is a response pattern which is preferably analyzed using a pattern recognition algorithm by comparing it to stored data obtained from a control sample whereby a significantly different response pattern of the test sample as compared the control sample is indicative of lung cancer or stages or subtypes thereof or enables the prediction of the response to certain therapies. In additional embodiments, where determining the stage or subtype of lung cancer is desired, the unknown test sample may be compared to a sample obtained from a subject known to be affricated with lung cancer (positive control). In accordance with these embodiments, a significantly different response pattern of the test sample might be detected when the test sample of a subject with adenocarcinoma is compared to a control sample of a subject with squamous cell lung cancer and vice versa.

The system and methods of the present invention enable the detection of a single volatile biomarker as well as the detection of a plurality of volatile biomarkers which characterize a particular subtype or stage of lung cancer. In certain embodiments, the volatile biomarker which is indicative of lung cancer is 1-octene.

The present invention encompasses the detection of a VOC profile characteristic of each of benign pulmonary nodules, malignant solitary nodules, small cell lung cancer, non-small cell lung cancer (early and advanced stages), adenocarcinoma and squamous cell carcinoma. Each possibility represents a separate embodiment of the present invention. Thus, according to the principles of the present invention, the differentiation between subjects having benign pulmonary nodules and subjects having malignant solitary nodules is afforded by the present invention. In addition, the present invention further provides the differentiation between subjects having small cell lung cancer (SCLC) and subjects having non-small cell lung cancer (NSCLC), and further provides the differentiation between subjects having NSCLC in an early stage and subjects having NSCLC in an advanced stage. In addition, the present invention further provides the differentiation between subjects having adenocarcinoma and subjects having squamous cell carcinoma. In addition, the present invention further provides the differentiation between subject having lung cancer and subjects having lung metastases including, but not limited to, renal clear cell cancer, melanoma, ovarian cancer, breast cancer and the like. Each possibility represents a separate embodiment of the present invention.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth. It should be noted that the term "and" or the term "or" is generally employed in its sense including "and/or" unless the content clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Materials and Methods

Breath collection Alveolar breath was collected using an 'offline' method that effectively separated the endogenous from the exogenous breath VOCs and further excluded the nasal entrainment. The method is described in details in Langmuir 2009; 25: 5411-5416; and Angew. Chem. Int. Ed. 2008; 47: 1703-1706, the contents of which are hereby incorporated by reference in their entirety. The tested individuals did not consume food for at least one hour and did not smoke for at least three hours prior to breath sampling. Alveolar exhaled breath was collected in chemically inert Mylar bags (Eco Medics) in a controlled manner, following a 3 minute procedure of lung wash as described in Euro. Resp. Soc. Monograph 2010; 49: 96-114; and Nature Nanotech 2009; 4: 669-673, the contents of which are hereby incorporated by reference in their entirety. The procedure was designed to prevent ambient contaminants and nasal entrainment of gas from entering the sampling bags. Each individual provided one or two Mylar bags (each having a volume of 750 ml). The content of each bag was transferred through an off-line procedure to tenax sorbent tubes (SKC) which is least affected by humidity. The tubes were kept at 4° C. in a clean environment. The tubes were then analyzed by GC-MS or by a tailor-made nano-sensor array as described hereinbelow.

Chemical analysis of the breath samples using GC-MS

The constituent VOCs in the breath samples and their concentration profiles were analyzed using gas chromatography/mass spectrometry (GC-MS; QP2010; Shimadzu Corporations) combined with Solid Phase Micro-Extraction (SPME). Eleven (11) benign and twenty eight (28) malignant samples were used for the chemical analysis. The collected samples were transferred into a thermal desorption device which was made of stainless steel (750 ml). The sorbent was heated to 270° C. for 10 min and at the same time was exposed to a Divinylbenzene/Carboxen/Polydimethylsiloxane (DVB/CAR/PDMS) SPME fiber (Sigma-Aldrich) which was used for pre-concentrating the VOCs in the breath samples. The extracted SPME fiber was inserted into the injector of the GC-MS column, which was set to 270° C. and operated in the splitless mode. The oven temperature profile was: 35° C., 5 min, 5° C./min to 180° C., 13.5° C./min to 290° C., 1 min. Capillary column SLC-5MS 5% phenyl methyl siloxane (30 m length, 0.25 mm i.d., 0.5 µm thickness) was used (purchased from Sigma-Aldrich). The column pressure was set to 23.4 kPa, and the column flow was 0.7 mL/min. GC-MS chromatogram analysis was performed using GC-MS Postrun Analysis (Shimadzu Corporations) version 2.53. The data was processed using the open source XCMS (version 1.22.1) package (http://metlin.scripps.edu/download/) which includes mass/charge (m/z) and retention times and the GC-MS analyzer software, which has been developed in the group of H. Haick and co-workers. Statistical tests were performed by SAS JMP, Version 8.0 (SAS Institute Inc., Cary, N.C., USA, 1989-2005) for Wilcoxon/Kruskal-Wallis tests. Identification of the VOCs was performed through spectral library match.

Breath analysis using the sensor array

The collected breath samples underwent blind analysis with a tailor-made sensor array which is composed of nanomaterials (hereinafter, nanoarray). The nanoarray is an artificial olfactory system based on an array of highly cross-reactive gas sensors that can identify and separate different VOC patterns, even when the VOCs are present at very low concentrations. The sensors are designed to have very little sensitivity to VOCs stemming from confounding factors such as age, gender, medication, smoking habits and environmental effects, including long-time exposure to clinical environment (Br. J. Cancer 2010; 103: 542-551). The nanoarray contained ten cross-reactive sensors that are based on spherical gold nanoparticles (GNPs; 3-6 nm core diameter) coated with 2-ethylhexanethiol, 2-amino-4-chlorobenzenethiol, 2-mercaptobenzimidazole, 2-mercaptobenzoazole, 2-nitro-4-trifluoromethylbenzenethiol, 3-methyl-1-butanethiol, 4-methoxy toluenethiol, dodecanethiol, hexanethiol and tert-dodecanethiol; and sensors that are based on single walled carbon nanotubes that are coated with polycrystalline polycyclic aromatic hydrocarbon layers containing a hydrophobic mesogen and terminated with ether groups, 2-decyl-tetradecane groups or 2-ethyl-hexane hydrophobic groups. In a complementary study, the nanoarray contained eighteen cross-reactive sensors. Sixteen sensors were chemiresistors based on spherical gold nanoparticles (GNPs; 3-6 nm core diameter) coated with hexanethiol, 2-ethylhexanethiol, 3-methyl-l-butanethiol, octadecylamine, decanethiol, dodecanethiol, 2-mercaptobenzoazole, 4-methoxy-toluenethiol, tert-dodecanethiol, 2-amino-4-chlorobenzenethiol, 2-mercaptobenzimidazole, benzylmercaptan, 2-nitro-4-trifluoro-methylbenzenethiol, 2-naphthalenethiol, 2-nitro-4-trifluoro-methylbenzenethiol and 2-mercaptobenzoazole; and two sensors were chemiresistors based on random networks of single-walled carbon nanotubes coated with polycyclic aromatic hydrocarbons which contained a hydrophobic mesogen and were terminated with (i) an ether group and with (ii) an 2-ethyl-hexane hydrophobic group.

1. Sensors of organically functionalized gold nanoparticles

The gold nanoparticles (GNPs) which were coated with a variety of organic ligands were used for measuring breath VOCs. The organic ligands provided the broadly cross-selective adsorption sites for the VOCs (Nature Nanotech 2009; 4: 669-673; Br. J. Cancer 2010; 103: 542-551; Br. J. Cancer 2011; 104: 1649-1655; Breast Cancer Res. Treat. 2010; 126: 791-796; MRS Bulletin 2010; 35: 797-803; Rev. Chem. Eng. 2011; 26: 171-179, the contents of which are hereby incorporated by reference in their entirety). The GNPs were synthesized as described in Nature Nanotech 2009; 4: 669-673; Br. J. Cancer 2010; 103: 542-551; Br. J. Cancer 2011; 104: 1649-1655; Breast Cancer Res. Treat. 2010; 126: 791-796; and Phys. Chem. C 2010; 114: 14042-14049, the contents of which are hereby incorporated by reference in their entirety. FIG. 1 shows a schematic representation of the GNP sensors which were formed by successively drop-casting the solutions of the organically functionalized gold nanoparticles onto 10 pairs of pre-prepared Ti/Au interdigitated electrodes. The left inset shows a representative transmission electron micrograph (TEM) of the organically functionalized GNPs in solution, which connects the electrodes and forms multiple paths between them. The metallic cores appear as dark dots which are separated one from the other by their capping organic ligands (a bright medium between adjacent dark dots). The right inset shows a schematic representation of films based on organically functionalized GNPs. In these films, the metallic particles provide the electric conductivity and the organic ligands provide sites for the sorption of analyte molecules (VOCs). In addition to their role as an adsorptive phase, the presence of well-defined organic spacers (i.e., capping ligands) enables the control over the inter-particle distance thereby obtaining nearly uniform inter-particle distances in the composite films. This enables to control signal and noise levels.

Macroscopically continuous chemiresistive layers were formed by drop-casting the solution onto semi-circular microelectronic transducers. The baseline resistance of the devices ranged from 1 kΩ-1 MΩ. The device was dried for 2 hours at ambient temperature and then baked at 50° C. in a vacuum oven for a period extending between 12 hours and a month, depending on the stabilization of the resistance. The microelectronic transducers contained ten pairs of circular interdigitated gold electrodes that were deposited by an electron-beam evaporator TFDS-870 (Vacuum Systems & Technologies, Petah Tikva, Israel) on a piece of silicon wafer capped with 1 μm thermal oxide (Silicon Quest International, Nevada, US). The outer diameter of the circular electrode area was 3mm, and the gap between two adjacent electrodes and the width of each electrode were both 20 μm.

2. Sensors of organically functionalized single walled carbon nanotubes

Figure 2:
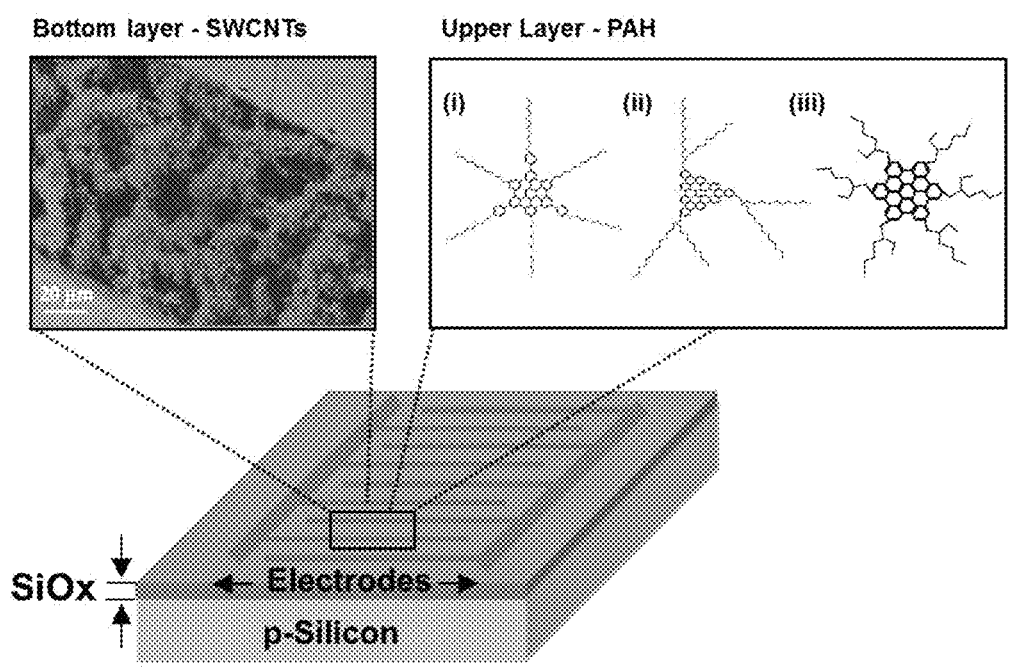
FIG. 2. Schematic representation of the PAH/SWCNT sensors (not drawn to scale). The left inset shows a representative scanning electron micrograph (SEM) of the random network of SWCNTs.

Sensors of single walled carbon nanotubes functionalized with polycyclic aromatic hydrocarbons (PAH/SWCNT) were prepared on device quality, degeneratively doped p-type Si(100) wafers capped with a 2 μm thick thermally grown $SiO_2$ insulating layer. Ten pairs of 4.5 mm width, interdigitated (ID) electrodes with an inter-electrode spacing of 100 μm were formed on the substrates by evaporation of 5 nm/40 nm Ti/Pd layer through a shadow mask. SWCNTs (from ARRY International LTD., Germany; ~30% metallic, ~70% semiconducting, average diameter: 1.5 nm, length: 7 μm) were dispersed in dimethylformamide (DMF, from Sigma Aldrich Ltd., >98% purity) using sonication for 15 min, resulting in a 0.02 wt% dispersion, which was then left for 0.5 hr in a 50 ml vial for sedimentation of large aggregates. The resulting homogeneous dispersion above the precipitate was then taken from the vial and further purified by ultracentrifugation for 25 min. The purification procedure was performed twice, to ensure that the majority of the aggregates and impurities are removed. Electrically continuous random network of SWCNTs were formed by drop-casting the SWCNT dispersion onto the pre-prepared ID electrodes. FIG. 2, left inset shows a scanning electron micrograph (SEM) of the random network of SWCNTs composing the bottom layer of the sensing film. After deposition, the devices were slowly dried overnight under ambient conditions to enhance the self-assembly of the SWCNTs and to evaporate the solvent. The procedure was repeated until a resistance of 100 KΩ-10 MΩ was obtained. As a reference, devices that included pristine PAH only exhibited a baseline resistance of 1-2 TΩ.

Nearly continuous, polycrystalline PAH layers containing a hydrophobic mesogen and terminated with ether groups, 2-decyl-tetradecane groups or 2-ethyl-hexane hydrophobic groups (ACS NANO 2011; 5: 6743-6753; and Langmuir 2009; 25: 5411-5416, the contents of which are hereby incorporated by reference in their entirety) were formed on top of the SWCNTs by drop casting 10 μL of $10^{-3}$ M PAH solution in toluene. FIG. 2, right inset shows a schematic representation of the different PAH molecules which were used to compose the upper organic film of the sensing material: (i) ether groups, (ii) 2-decyl-tetradecane, and (iii) 2-ethyl-hexane hydrophobic groups. These molecules self-assemble into long molecular stacks with large, electron-rich, semiconducting cores, which guarantee good charge carrier transport along the molecular stacking direction and a relatively insulating periphery. Furthermore, the nanometer thick PAH columns can easily form 3D, micrometer-sized, sponge-like structures with a high surface-to-volume ratio (Adv. Mater. 2008; 14: 2684-2689; Nature Mater. 2009; 8: 421-426; J. Am. Chem. Soc. 2009; 131: 4439-4448; and Angew. Chem. Int. Ed. 2008; 47: 1703-1706, the contents of which are hereby incorporated by reference in their entirety). After the fabrication, the devices were slowly dried under ambient conditions for 2-5 hours to enhance the self-assembly of the PAH molecules and to evaporate residual solvent. The baseline resistance of the PAH/SWCNT sensor generally ranged between ~0.5-1 kΩ.

Exposure of sensors to breath samples

The fabricated sensors were mounted on a custom PTFE circuit board inside a stainless steel test chamber with a volume of 100 cm³. The sampling system delivered pulses of the breath samples from the thermal desorption device to the sensors. The chamber was evacuated between exposures. An Agilent multifunction switch 34980 was used to measure the resistance of all sensors as a function of time. Typically, the sensors' responses were recorded for 5 min in (40 mtorr) vacuum, followed by 5 min under breath sample exposure, followed by another 5 min in vacuum. All samples received from the clinical collaborators (University of Colorado Cancer Center and Denver Veterans Affairs Medical Center) were tagged with a barcode at the collection site. The tubes were stored at 4° C. in a clean environment. The sorbent tubes were then shipped to the Technion-IIT labs (Haifa, Israel) for GC-MS and nanoarray analysis. The results of the analysis were then conjugated with the relevant clinical data.

Statistical analysis

The Wilcoxon test was applied to the extracted features to check for a significant difference between the average sensing signals of the various categories tested. Data classification was performed by employing the Discriminant Factor Analysis (DFA) algorithm. DFA is a supervised linear method that is supplied with the classification information regarding every measurement in the training set. DFA finds new orthogonal axes (canonical variables) as a linear combination of the input variables, computing these factors to minimize the variance within each class and maximize the variance between classes. The accuracy of the DFA blind analysis was further confirmed by employing the leave-one-out cross-validation method. Given n measurements, the pattern recognition model was computed n times using n-1 training vectors. The vector which was left out during the training phase (the validation vector, which is unseen by the algorithm during the training phase, thus being completely new for the built model) was then projected onto the built model, producing a classification output. All possibilities of leave-one-sample-out were considered, and the classification accuracy was estimated as the average performance over the entire n tests. Statistically significant differences between the first-discriminant scores were studied using the Wilcoxon test. Sensitivity, specificity and accuracy were calculated through leave-one-out cross-validation. Statistical tests were performed by SAS JMP, Version 8.0.

Example 1

Analysis of Breath Samples of Individuals With Malignant and Benign SPNs

Figure 3:
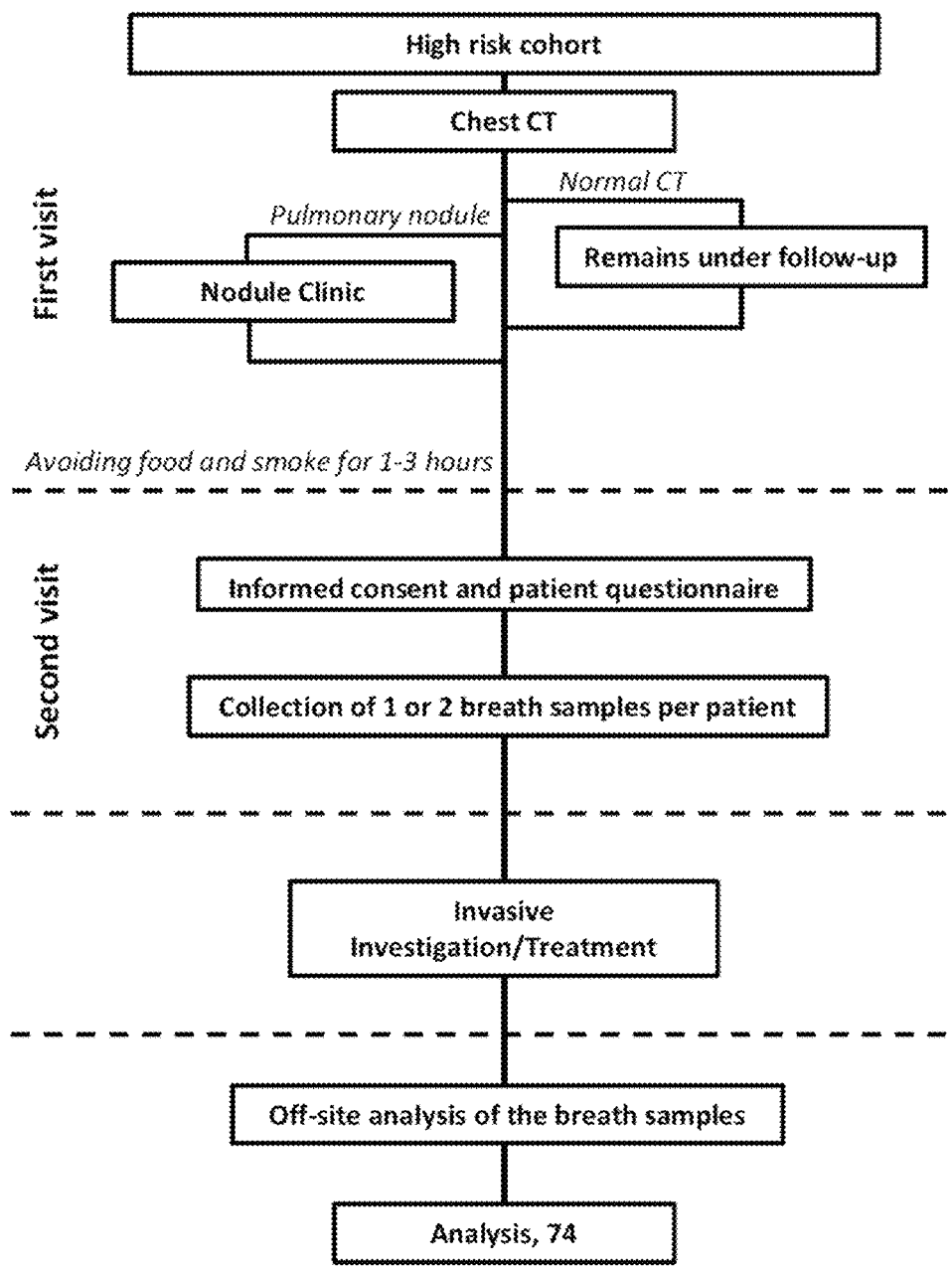
FIG. 3. Timeline for patient recruitment, assessment of clinical data, breath sampling and initiation of treatment.

Seventy-four (74) individuals with solitary pulmonary nodules (SPNs) were examined. Samples of two (2) individuals were excluded due to a technical problem. The individuals attended subspecialty referral clinics at the University of Colorado Cancer Center (Aurora, CO, USA) and Denver Veterans Affairs Medical Center (Denver, Colo., USA) from March 2009 to May 2010. The Colorado IRB granted ethical approval for the study, and the clinical trial was registered at Clinicaltrials.gov (registration No.: NCT01386203). After breath sampling, all individuals underwent conventional invasive diagnostic procedures, including bronchoscopy, wedge resection and/or lobectomy as was recommended clinically for final diagnosis. The conventional diagnosis served as a standard reference for the breath testing and subsequent treatment. Lung cancer was diagnosed in 53 individuals and benign conditions were found in 19 individuals. Individuals without a definitive histologic diagnosis were followed by serial CT imaging, and final diagnosis was reconfirmed in August 2011. Nodules which either regressed or remained stable over a 24 month period were considered benign. The clinical details of the study population are summarized in Table 1. Baseline epidemiology, smoking history and co-morbidities were similar in both groups (malignant and benign). The two groups were relatively well-matched with respect to their ages: 64.9±7.2 years for individuals with malignant nodules vs. 60.8±6.8 years for individuals with benign nodules (p = 0.038). Thirty-six (36) individuals underwent bronchoscopy and thirty six (36) underwent a surgical procedure. Forty-seven (47) individuals had NSCLC (30 adenocarcinoma, 13 squamous cell carcinoma, 2 large cell carcinoma and 2 poorly differentiated carcinoma) and 6 individuals had SCLC. Thirty (30) individuals had early stage disease (Stage I-II or limited SCLC) and 23 had advanced stage disease (Stage III/IV or extensive SCLC; Table 1). Histological examination identified thirteen (13) individuals with granulomas or fibrotic tissue, one (1) individual with alveolar hyperplasia, and five (5) individuals with infectious/inflammatory histologies, among the benign group (N=19). Nodule size was significantly larger in the malignant group (mean diameter+/−SD=2.7±1.7 cm for lung cancer vs. 1.56±1.3 cm for benign, p=0.004). FIG. 3 shows the timeline for recruitment, clinical diagnosis, breath testing and treatment of the individuals. All breath samples received from the clinical collaborators (University of Colorado Cancer Center) were tagged with a barcode. The samples were evaluated in a blind analysis at the Technion-IIT.

The results of the analysis were then conjugated with the relevant clinical data provided by the clinical collaborators at the end of the analysis.

TABLE 1

Clinical characteristics of the tested individuals

| | Benign Nodules (N = 19) | | Malignant Nodules (N = 53) | | p-value (<0.05) |
|---|---|---|---|---|---|
| Age (years) | 60.8 ± 6.8 | | 64.9 ± 7.2 | | 0.038 |
| BMI (kg/m$^2$)[1] | 26.2 ± 5.1 | | 27.4 ± 7.2 | | NS[5] |
| Males | 15 (79%) | | 31 (58%) | | NS[5] |
| Active Smokers | 6 (32%) | | 19 (36%) | | NS[5] |
| Former Smokers | 11 (58%) | | 26 (49%) | | NS[5] |
| Never Smokers | 2 (11%) | | 8 (15%) | | NS[5] |
| PY (Total)[2] | 40.6 ± 34.4 | | 40.5 ± 27.0 | | NS[5] |
| COPD[3] | 10 (52%) | | 26 (49%) | | NS[5] |
| IHD[4] | 7 (37%) | | 22 (42%) | | NS[5] |
| Nodule Size (cm) | 1.56 ± 1.3 | | 2.7 ± 1.7 | | 0.004 |
| Diagnostic Procedure | | | | | |
| Bronchoscopy | 16 | | 20 | | |
| Wedge/Lobectomy | 3 | | 33 | | |
| Etiology | Non-Cancerous | 13 | NSCLC: | 47 | |
| | Atypical Alveolar Hyperplasia | 1 | Adenocarcinoma Squamous | 30 13 | |

TABLE 1-continued

Clinical characteristics of the tested individuals

| | | | Benign Nodules (N = 19) | | Malignant Nodules (N = 53) | | p-value (<0.05) |
|---|---|---|---|---|---|---|---|
| | | Infectious/Inflammation | 5 | Large Cell | 2 | | |
| | | | | Poorly Diff. | 2 | | |
| | | | | SCLC | 6 | | |
| Stage | | | | NSCLC: | | | |
| | | | | Stage I | 23 | | |
| | | | | Stage II | 4 | | |
| | | | | Stage III | 10 | | |
| | | | | Stage IV | 10 | | |
| | | | | SCLC: | | | |
| | | | | Limited | 3 | | |
| | | | | Extensive | 3 | | |

[1]BMI: Body Mass Index
[2]PY: Pack Years
[3]COPD: Chronic Obstructive Pulmonary Disease
[4]IHD: Ischemic Heart Disease
[5]NS: No significant changes between the groups were identified

Example 2

Chemical Analysis of Breath Samples using GC-MS

Figure 4A:
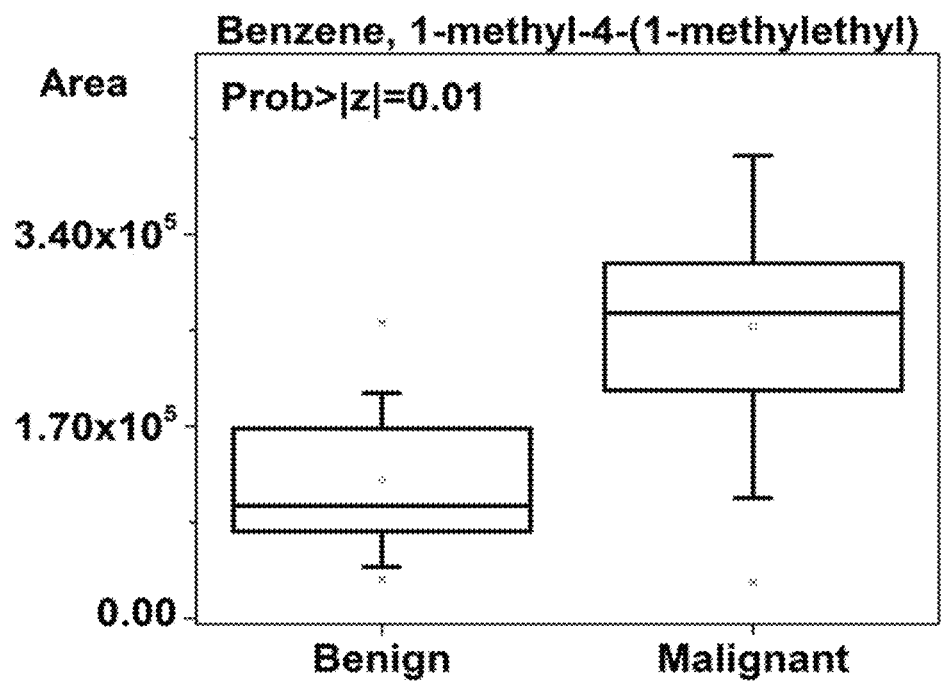
FIGS. 4A-4B. Two breath biomarkers for differentiating malignant lung nodules from benign lung nodules. (4A) 1-methyl-4-(1-methylethyl) benzene, and (4B) 1-octene.
Figure 4B:
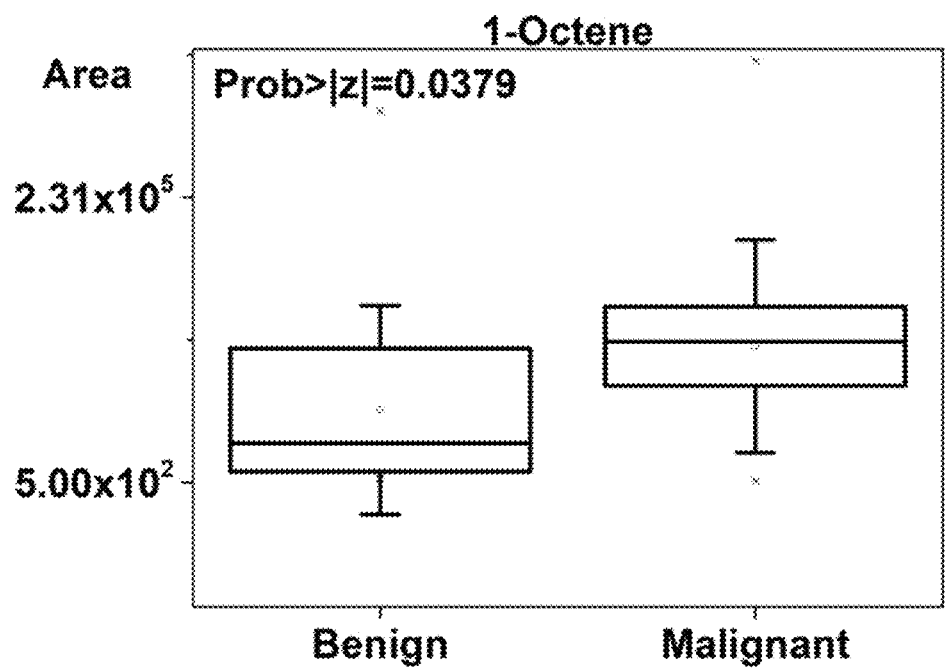
Figure 5:
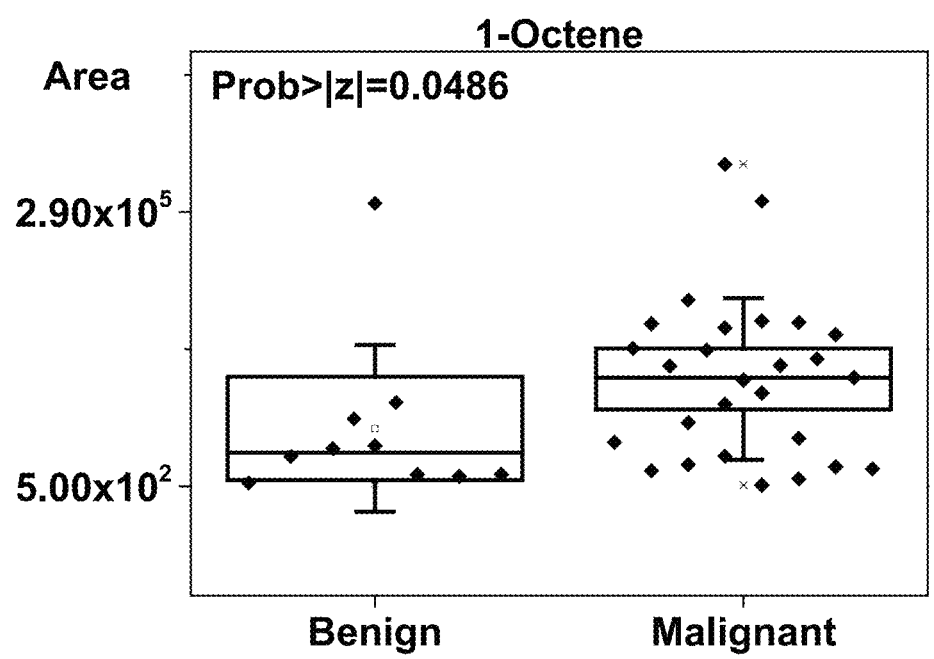
FIG. 5. 1-octene as a breath biomarker for differentiating malignant lung nodules from benign lung nodules.

Volatile organic compounds (VOCs) that can serve as biomarkers for solitary pulmonary nodules in breath samples were identified and their relative compositions were determined using GC-MS in conjugation with solid phase microextraction (SPME). The GC-MS technique is based on spectrum and retention times (BMC Cancer 2009; 9: 348; and Clin. Chem. Lab Med. 2009; 47: 550-560). Twenty eight (28) samples from individuals with malignant nodules (25 NSCLC and 3 SCLC) and eleven (11) samples from individuals with benign nodules were analyzed. Hundreds of different VOCs per breath sample were identified, of which approximately 200 VOCs had main masses in the range of 33 to 282 m/z and retention times between 1.8 and 42.8 minutes. Non-parametric Wilcoxon/Kruskal-Wallis tests identified two VOCs that appeared at higher concentrations in individuals having lung cancer, compared to individuals with benign nodules, namely 1-methyl-4-(1-methylethyl)-benzene and 1-octene (FIGS. 4A and 4B, respectively; Table 2). In a complementary study, 1-octene (CAS number: 111-66-0; m/z=83; average retention time: 11.18 min; p=0.049 in Wilcoxon nonparametric method) was identified at higher concentrations in individuals having lung cancer as compared to individuals having benign nodules (N=39: Malignant=28 and Benign=11). FIG. 5 shows the area under peak for each individual sample and the ANOVA analysis. The positions of the mean values for benign and malignant states are marked with □, the boxes correspond to their 95% confidence limits, and the error bars correspond to the standard deviation. The exact value of the peak area of each sample is provided in Table 3. It has been shown that 1-octene undergoes oxidation by the cytochrome P450-associated enzyme activity (Cell 2008; 134: 703-707). These enzymes play a central role in the metabolic activation of various xenobiotics. Without being bound by any theory or mechanism of action, changes in gene expression or enzyme activity in cases of lung cancer might affect the concentration of 1-octene in the body (Langmuir 2009; 25: 5411-5416; and Chest 2003; 123: 2115-2123). 1-methyl-4-(1-methylethyl)-benzene is an environmental (exogenic) VOC. This VOC is metabolized within a few hours following its entry into the human body via an inhalation exposure route either from contaminated environmental air and/or from tobacco smoke (Lancet 1999; 353: 1930-1933; N. Engl. J. Med. 2011; 365: 395-409; and Anal. Bioanal. Chem. 2006; 386: 1059-1073). Without being bound by any theory or mechanism of action, it is possible that lung cancer patients, who have been exposed to excessive smoking and/or have experienced continuous occupational exposure to benzene compounds, might have higher benzene concentrations in exhaled breath resulting from benzene uptake in the fatty tissues.

The GC-MS analysis did not show any discrimination between early stage and advanced stage disease of the non-small cell lung cancer (NSCLC). While many VOCs could be associated with the stage of the disease, the difference between the corresponding VOC concentrations were not statistically significant (p>0.05). Without being bound by any theory or mechanism of action, the failure of the GC-MS analysis to detect altered VOC production between early stage and advanced stage NSCLC could be attributed to the following explanations. First, the GC-MS data do not account for all VOCs present in the exhaled breath samples, because of the pre-concentration technique (e.g., SPME) that is used. Second, the concentration of breath VOCs might be lower than the GC-MS/SPME limit of detection (1-20 ppb; BMC Cancer 2009; 9: 348). Comparative GC-MS analysis failed to show any discrimination between sub-histologies of NSCLC. Of note is that GC-MS analysis was not performed for the NSCLC and SCLC groups due to insufficient number of samples of the SCLC group.

TABLE 2

VOCs from exhaled breath samples which were identified in benign and malignant nodules with statistically significant difference

| Retention time (min) | m/z | VOC | Trend in Cancer | p-values[1] |
|---|---|---|---|---|
| 11.18 | 83 | 1-octene | Up | 0.038 |
| 20.37 | 119 | 1-methyl-4-(1-methylethyl)-benzene | Up | 0.010 |

[1]Wilcoxon non-parametric method

TABLE 3

Peak area of samples from individuals having benign or malignant nodules

| Category | Sample name | Area under peak |
|---|---|---|
| Benign | 117-2-t | 13387.38 |
| Benign | 143-2-t | 43427.74 |
| Benign | B-118-2-t | 40272.59 |
| Benign | COPD-110-2-t | 89043.14 |
| Benign | COPD-116-2-t | 12861.94 |
| Benign | COPD-133-2-t | 32050.43 |
| Benign | COPD-30-4-t | 11077.31 |
| Benign | COPD-40-4-t | 3988.337 |
| Benign | COPD-57-4-t | 71835 |
| Benign | VC-108-2-t | 299711 |
| Malignant | P-103-2-t | 12979.6 |
| Malignant | P-104-2-t | 302046.5 |
| Malignant | P-114-2-t | 340815.5 |
| Malignant | P-119-2-t | 1861.703 |
| Malignant | P-122-2-t | 32212.48 |
| Malignant | P-123-2-t | 8378.869 |
| Malignant | P-131-2-t | 23504.67 |
| Malignant | P-132-2-t | 175336.5 |
| Malignant | P-138-2-t | 112885.5 |
| Malignant | P-141-2-t | 21090 |
| Malignant | P-24-4-t | 99031.76 |
| Malignant | P-31-4-t | 87261 |
| Malignant | P-33-2-t | 16927.81 |
| Malignant | P-36-4-t | 167969 |
| Malignant | P-37-4-t | 144478.5 |
| Malignant | P-38-4-t | 128378.5 |
| Malignant | P-39-4-t | 127654 |
| Malignant | P-42-4-t | 173735.5 |
| Malignant | P-60-2-t | 135290.7 |
| Malignant | P-62-2-t | 146325 |
| Malignant | P-66-1-t | 197362.5 |
| Malignant | P-71-1-t | 115416.5 |
| Malignant | P-74-1-t | 51204.12 |
| Malignant | P-92-2-t | 67893.23 |
| Malignant | P-97-2-t | 160770.5 |
| Malignant | SCLC-100-2-t | 172197.5 |
| Malignant | SCLC-91-2-t | 18967.53 |
| Malignant | SCLC-96-2-t | 46979.29 |

Thus, 1-octene is found in significantly higher concentrations in the breath of individuals with malignancies as compared to individuals which have benign nodules. Accordingly, 1-octene can be used as a breath biomarker for lung cancer.

Example 3

Nanoarray Analysis of Breath Samples

Figure 6A:
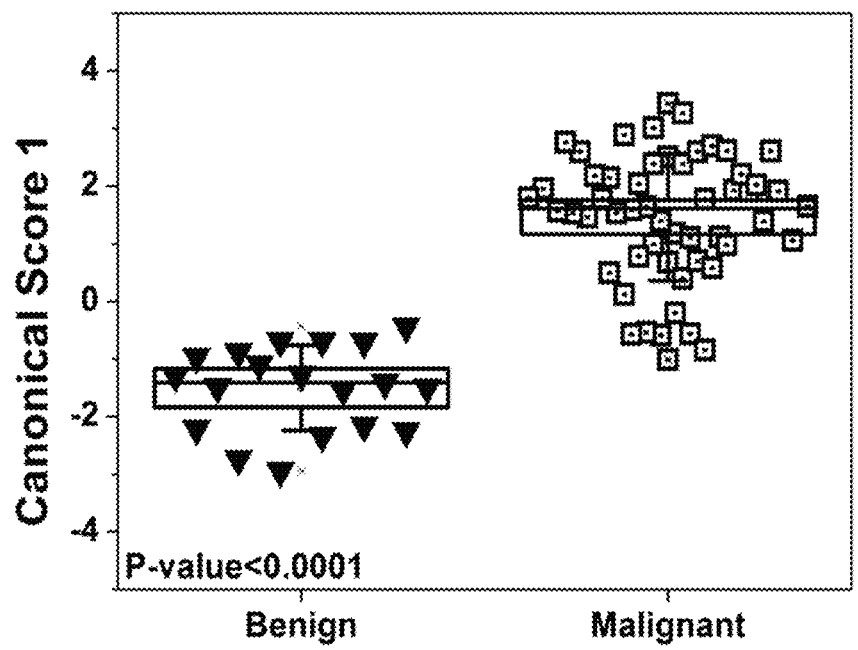
FIGS. 6A-6B. (6A) Graphical representation of the first canonical score values for patients with benign nodules and malignant nodules that were obtained from a nanoarray containing organically functionalized 5-nm gold nanoparticle sensors and an organically-functionalized carbon nanotube sensor. (6B) Receiver operating characteristic (ROC) curve for the discrimination between malignant and benign pulmonary nodules (PNs). The area under the curve (AUC) is 0.986.

In order to differentiate between collective VOC patterns of malignant and benign lung nodules, a DFA model using tailor-made nanoarrays was utilized. Seventy (70) of the 74 breath samples collected were examined. All sensors responded rapidly and differently to small changes in VOC concentration and provided a consistent output which was specific to a given breath exposure. Two breath samples were excluded from the analysis due to technical failures of the electrical readout of the sensing signals during measurement. Accordingly, a Discriminant Factor Analysis (DFA) model was based on the sixty eight (68) breath samples collected for nanoarray measurement and subsequent analysis. The nanoarray analysis provided good discrimination between individuals with malignant nodules and individuals with benign nodules (FIG. 6A). Full separation was achieved along the first canonical score (The confidence intervals are significantly separated, namely p-values<0.0001 by Wilcoxon test). Leave-one-out cross-validation was performed in order to check the accuracy of the DFA model. The first DFA model had a classification success of 86±4% for sensitivity, 96±4% for specificity, and 88±3% for accuracy (Table 4). ROC analysis has yielded AUC of 0.986 (FIG. 6B; Table 4) for the discrimination between benign and malignant conditions. The identification of the collective patterns was supported by the observation of statistically significant differences between the sub-populations in the average composition of the exhaled breath (FIG. 6A). Each point represents one patient. The positions of the canonical score mean values are marked with □, the boxes correspond to their 95% confidence limits, and the error bars corresponds to the standard deviation of the first canonical score values. The sensors that were used: six sensors of GNPs coated with 4-methoxy-toluenethiol; 2-mercaptobenzimidazole; hexanethiol; 2-amino-4-chlorobenzenethiol; 2-ethylhexanethiol; and 3-methyl-1-butanethiol; and one sensor of SWCNTs coated with HBC-$C_{6,2}$. The results support future incorporation of the breath analysis using nanoarrays with the conventional low dose CT protocol for improving the specificity of the screening program (FIG. 7).

TABLE 4

Sensitivity, specificity, and accuracy of the nanoarray analysis (from leave-one-out cross-validation) and the AUC of the ROC curve analysis

|  | Sensitivity (%) | Specificity (%) | Accuracy (%) | ROC AUC |
|---|---|---|---|---|
| Malignant/Benign | 86 ± 4 | 96 ± 4 | 88 ± 3 | 0.986 |
| Adeno/squamous | 92 ± 8 | 78 ± 7 | 88 ± 3 | 0.974 |
| Early/Advanced NSCLC | 86 ± 3 | 88 ± 6 | 88 ± 2 | 0.961 |

Figure 8:
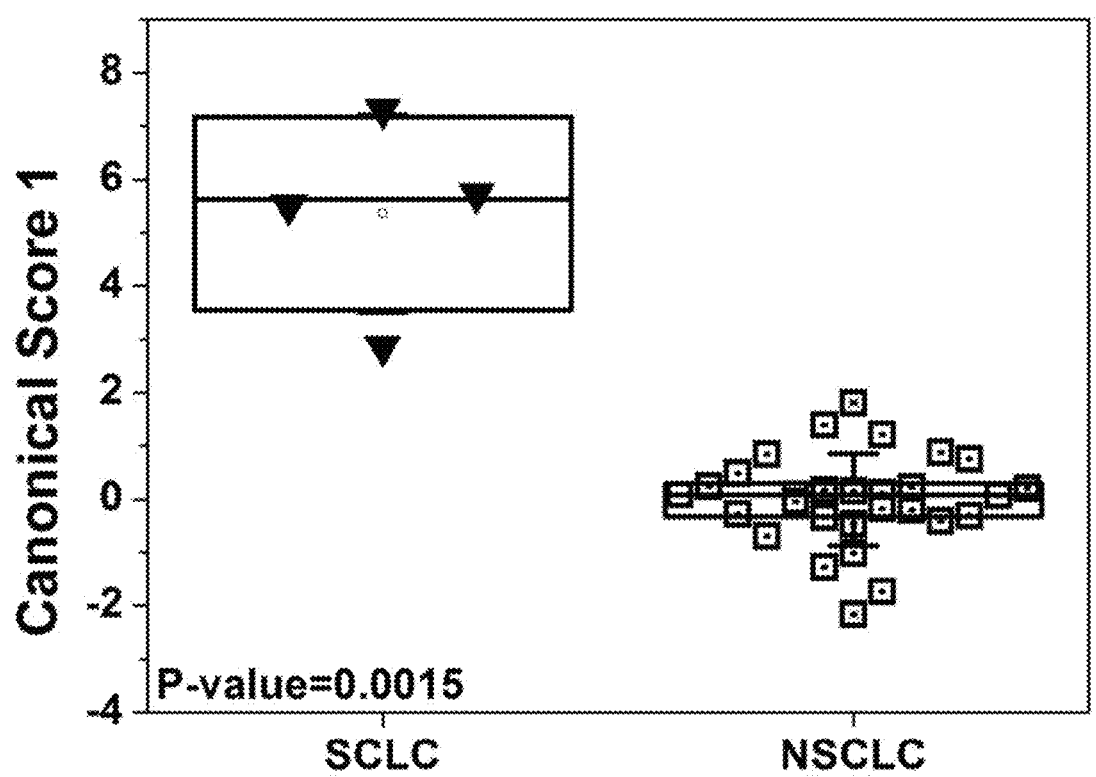
FIG. 8. Graphical representation of the first canonical score values of individuals with malignant nodules differentiating between NSCLC and SCLC using a sensor array containing four gold nanoparticle sensors.

The nanoarray analysis also provided good differentiation between sub-histology states of lung cancer. FIG. 8 shows good discrimination between small cell and non-small cell lung cancer which constitute sub-populations of individuals with malignant nodules.

Each point represents one patient (one SCLC patient was excluded due to a technical failure). The positions of the canonical score mean values are marked with □, the boxes correspond to their 95% confidence limits, and the error bars corresponds to the standard deviation of the first canonical score values. The two sub-populations were completely separated along the first canonical score, with no overlap between the clusters (The confidence intervals are significantly separated, namely p-values=0.0015 by Wilcoxon test). Cross-validation of the blind analysis revealed sensitivity of 75±4%, specificity of 97±1% and accuracy of 94±1%. Without being bound by any theory or mechanism of action, these two histologically different subtypes of lung cancer have significant differences in the growth rate and metabolism. Specifically, the quantity and variety of metabolites released by small cell lung cancer (SCLC) is larger than the quantity and variety of metabolites released by non-small cell lung cancer (NSCLC) because SCLC cells are rapidly dividing cells that require more adenosine triphosphate (ATP), nucleotides, fatty acids, membrane lipids and proteins (Cell 2008; 134: 703-707).

Figure 9A:
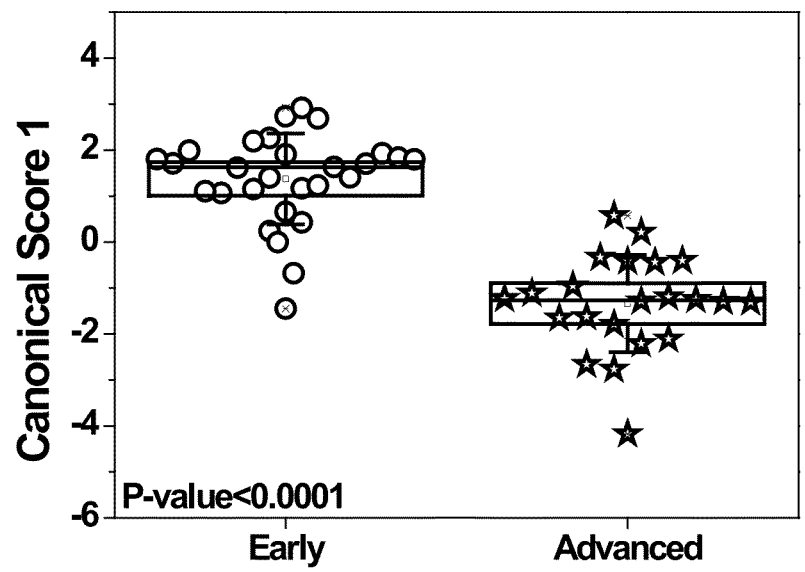
FIGS. 9A-9B. (9A) Graphical representation of the first canonical score values for patients with early stage or advanced stage NSCLC nodules that were obtained from a chemical nanoarray containing seven gold nanoparticle sensors and an organically-functionalized carbon nanotube sensor. (6B) Receiver operating characteristic (ROC) curve for the discrimination between early and advanced stages of NSCLC. The area under the curve (AUC) is 0.961.
Figure 9B:
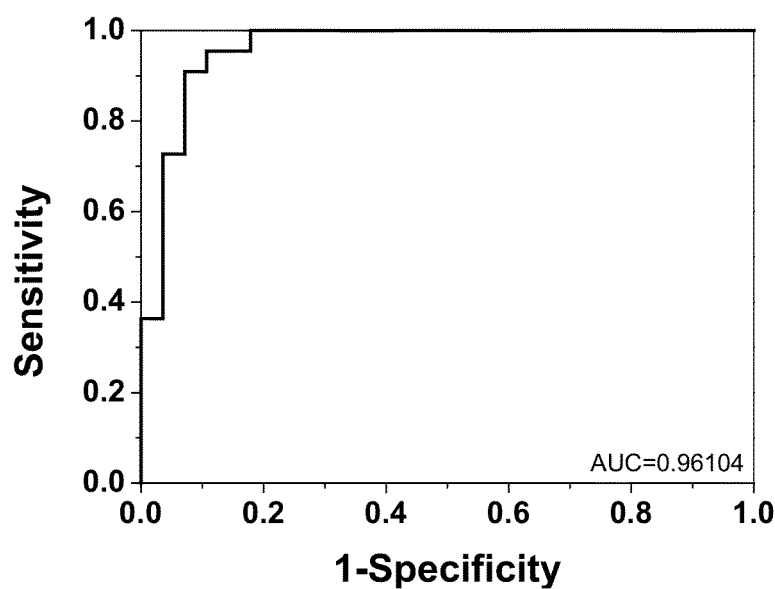

Within the non-small cell lung cancer (NSCLC) group, excellent differentiation was obtained between early and advanced stages (FIG. 9A). Each point represents one patient. The positions of the canonical score mean values are marked with □, the boxes correspond to their 95% confidence limits, and the error bars corresponds to the standard deviation of the first canonical score values. The confidence intervals are significantly separated (p-values<0.0001 by Wilcoxon test). Cross-validation of the blind analysis revealed sensitivity of 86±3%, specificity of 88±6% and accuracy of 88±2% (Table 4). The corresponding ROC curve is shown in FIG. 9B. The results show that breath analysis using nanoarray in conjunction with a pattern recognition algorithm provides a sensitive and specific test for cancerous solitary pulmonary nodules detection. This technology could serve as a primary and/or a secondary screener for PN-positive patients after low-dose CT, and might avoid delay in performing an invasive investigation when cancer is suspected with a relatively high level of confidence.

Example 4

Comparative Results Using a GNP-Based Nanoarray vs. GNP/SWCNTs-Based Nanoarray

The ability of the nanoarray based on organically functionalized GNPs combined with SWCNTs functionalized with polycyclic aromatic hydrocarbons to differentiate between populations of malignant and benign SPNs and sub-populations of lung cancer was compared to that of a nanoarray based on organically functionalized GNPs solely.

Figure 6B:
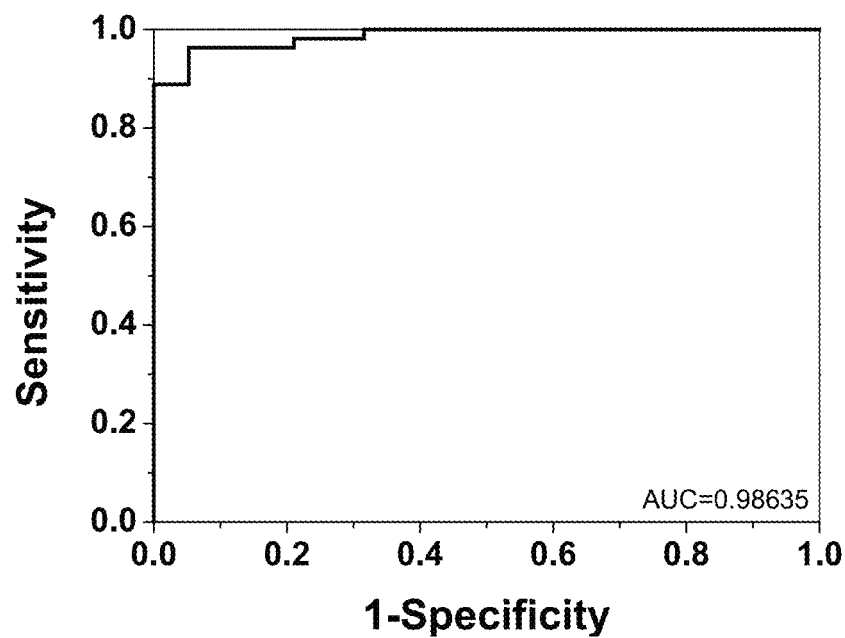
Figure 7:
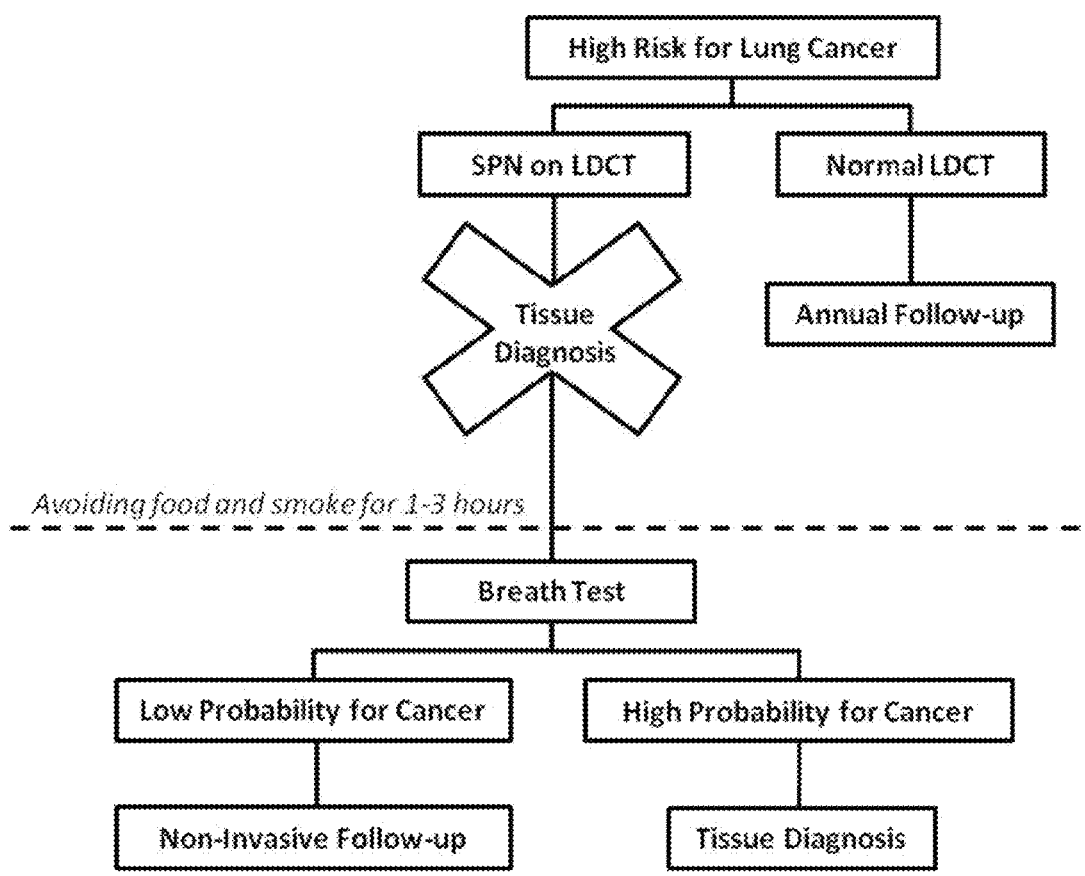
FIG. 7. A proposed algorithm incorporating non-invasive breath analysis prior to tissue diagnosis using the low dose CT screening protocol.
Figure 10:
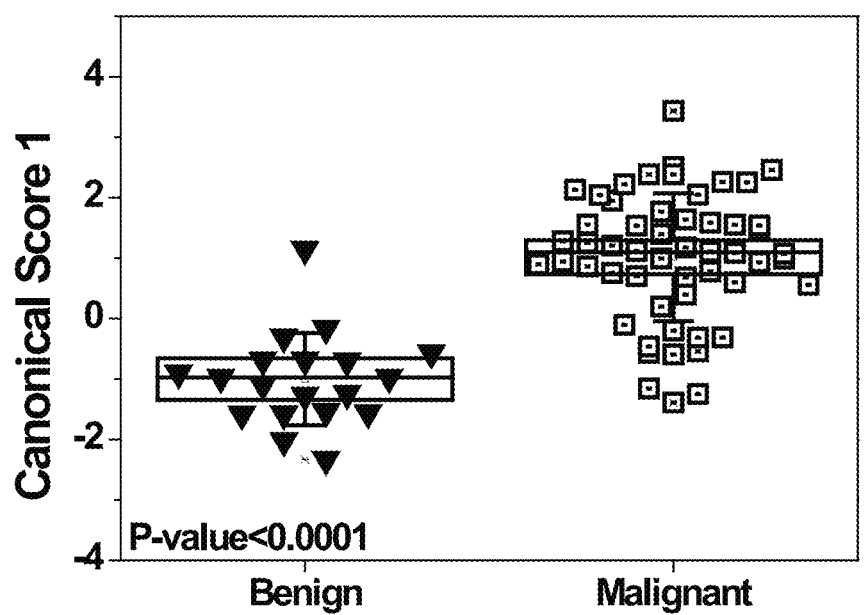
FIG. 10. Graphical representation of the first canonical score values for patients with benign nodules and malignant nodules that were obtained from a nanoarray containing organically functionalized 5-nm gold nanoparticle sensors solely.
Figure 11A:
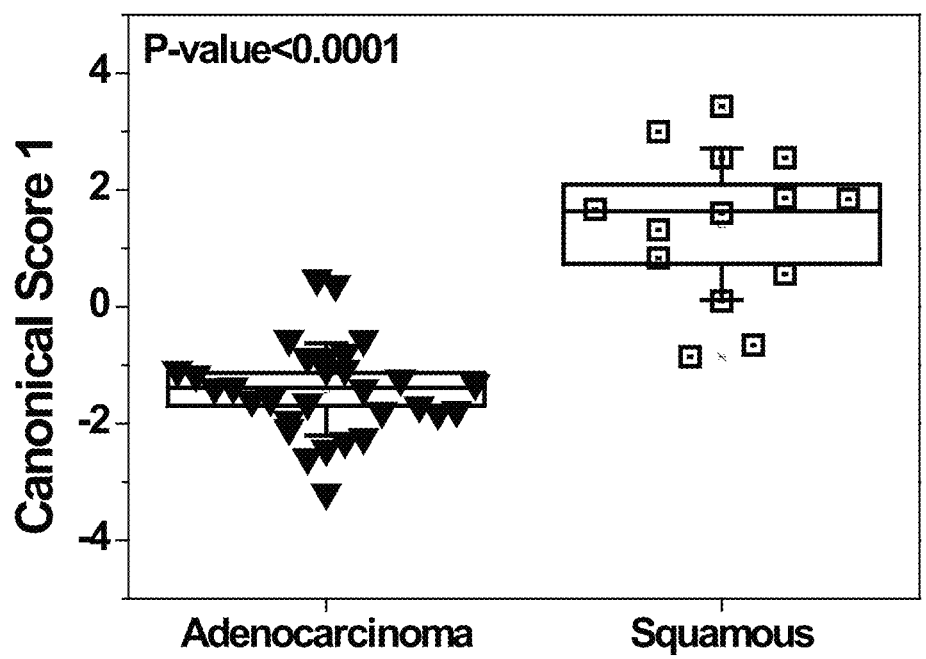
FIGS. 11A-11B. (11A) Graphical representation of the first canonical score values for patients with malignant nodules differentiating between adenocarcinoma and squamous cell lung cancer, obtained from a chemical nanoarray containing gold nanoparticle sensors. (6B) Receiver operating characteristic (ROC) curve for the discrimination between adenocarcinoma and squamous cell lung cancer. The area under the curve (AUC) is 0.974.
Figure 11B:
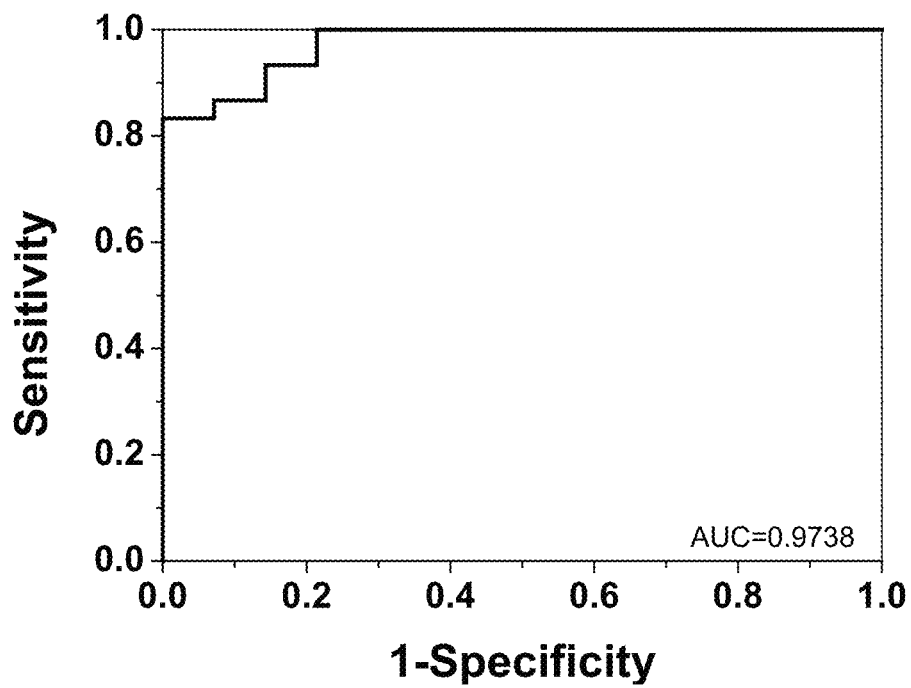

The analysis of the measurements of a nanoarray containing organically functionalized spherical gold nanoparticle sensors and organically functionalized carbon nanotube sensors provided excellent differentiation between malignant SPNs and benign SPNs (FIGS. 6A and 6B; Table 4). Breath analysis using the same GNP sensors without the PAH functionalized SWCNTs sensor revealed sensitivity of 80±1%, specificity of 88±12% and accuracy of 82±3% (FIG. 10). A further differentiation between adeno- and squamous cell carcinoma was performed using a sensor array which contained sensors of GNPs coated with benzylmercaptan; 2-nitro-4-trifluoro-methylbenzenethiol; 2-naphthalenethiol; 4-methoxy-toluenethiol; octadecylamine; decanethiol; 2-ethylhexanethiol; and 2-mercaptobenzoazole and no SWCNTs sensors. FIG. 11A shows good differentiation between adeno- and squamous- cell carcinomas within the test group of individuals with malignant nodules. The two sub-populations were completely separated along the first canonical score, with no overlap between the clusters (p<0.0001). Cross-validation of the analysis yielded an accuracy of 88±3% (Table 4). The corresponding ROC curve is shown in FIG. 11B.

Figure 12:
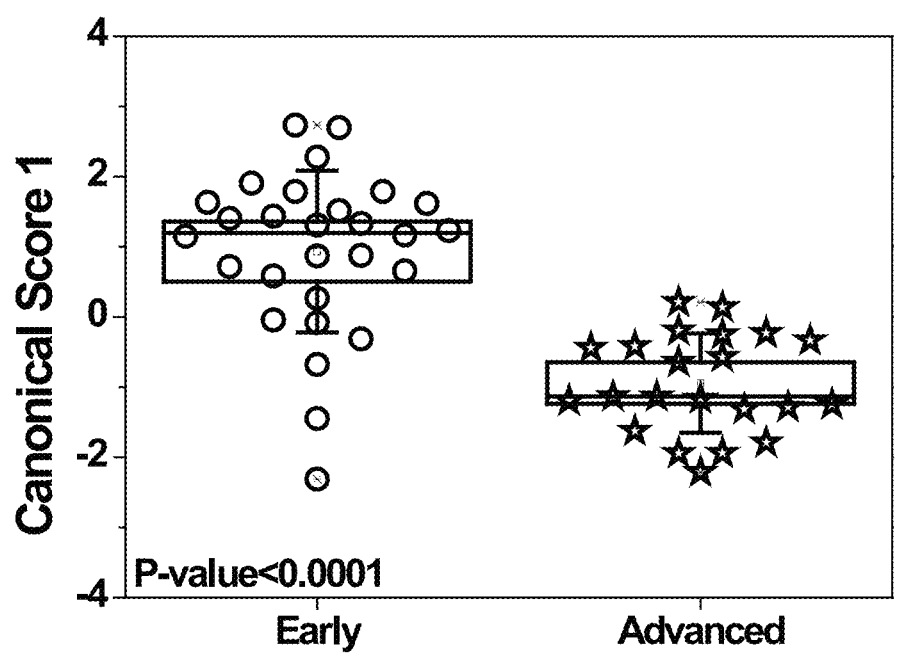
FIG. 12. Graphical representation of the first canonical score values for patients with early stage or advanced stage NSCLC nodules that were obtained from a chemical nanoarray containing seven gold nanoparticle sensors solely.

As detailed above, excellent differentiation was obtained between breath samples of early and advanced stages of non-small cell lung cancer (NSCLC) using a sensor array which contained a combination of sensors of GNPs functionalized with 2-nitro-4-trifluoro-methylbenzenethiol; 2-mercaptobenzoazole; dodecanethiol; octadecylamine; 4-methoxy-toluenethiol; tert-dodecanethiol; hexanethiol and a sensor of SWCNTs functionalized with a polycyclic aromatic hydrocarbon (PAH-1). Breath analysis using the same GNP sensors without the functionalized SWCNTs sensor revealed sensitivity of 86±3%, specificity of 88±6% and accuracy of 88±2% (FIG. 12).

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A system for diagnosing, monitoring or prognosing lung cancer or stages or subtypes thereof or predicting a patient's response to a treatment regimen, the system comprising:
an apparatus comprising at least one sensor comprising single walled carbon nanotubes coated with polycyclic aromatic hydrocarbons and at least one electrical sensor comprising metal nanoparticles coated with an organic coating;
a detector; and
a processing unit comprising a pattern recognition analyzer, wherein the pattern recognition analyzer receives sensor output signals and compares them to stored data so as to enable the diagnosis, monitoring or prognosis of lung cancer or stages or subtypes thereof or the prediction of a patient's response to a treatment regimen.

2. The system according to claim 1, wherein the single walled carbon nanotubes are organized in a random network configuration.

3. The system according to claim 1, wherein the polycyclic aromatic hydrocarbons are selected from arenes, polyarenes, and combinations thereof.

4. The system according to claim 3, wherein the arenes or polyarenes are selected from the group consisting of naphthalene, acenaphtene, anthracene, phenanthrene, pyrene, benzo[a]pyrene, chrysene, fluoranthene, $C_{18}$-$C_{180}$ graphenes and combinations thereof.

5. The system according to claim 3, wherein the arenes or polyarenes are substituted with one or more hydrophobic or hydrophilic carbon chains or at least one functional group selected from ester, ether, alcohol, amine, imine, amide, ammonium, keto, aldehyde, halogen (halo), pyridyl, phosphate, thiol, sulfonate, sulfonyl, hydroxyl, carboxylate, carboxyl, and carbonate groups.

6. The system according to claim 1, wherein the polycyclic aromatic hydrocarbons comprise hexa-peri-hexabenzocoronene (HBC) molecules which are unsubstituted or substituted by any one of 2-ethyl-hexyl (HBC-$C_{6,2}$), 2-hexyldecane (HBC-$C_{10,6}$), 2-decyl tetradecane (HBC-$C_{14,10}$), and dodecane (HBC-$C_{12}$).

7. The system according to claim 1, wherein the metal nanoparticles are selected from the group consisting of Au, Ag, Ni, Co, Pt, Pd, Cu, and Al nanoparticles and combinations thereof.

8. The system according to claim 1, wherein the organic coating of the metal nanoparticles comprises compounds selected from the group consisting of alkylthiols, arylthiols, alkylarylthiols, alkylthiolates, ω-functionalized alkanethiolates, arenethiolates, (γ-mercaptopropyl)tri-methyloxysilane, dialkyl disulfides and combinations and derivatives thereof.

9. The system according to claim 1, wherein the organic coating of the metal nanoparticles comprises compounds selected from the group consisting of hexanethiol, 2-ethylhexanethiol, 3-methyl-1-butanethiol, octadecylamine, decanethiol, dodecanethiol, 2-mercaptobenzoazole, 4-methoxy-toluenethiol, tert-dodecanethiol, 2-amino-4-chlorobenzenethiol, 2-mercaptobenzimidazole, benzylmercaptan, 2-nitro-4-trifluoro-methylbenzenethiol, 2-naphthalenethiol, 2-nitro-4-trifluoro-methylbenzenethiol, and combinations thereof.

10. The system according to claim 1, wherein the at least one sensor is configured in a form selected from the group consisting of a capacitive sensor, a resistive sensor, a chemiresistive sensor, an impedance sensor, and a field effect transistor sensor.

11. The system according to claim 1, wherein the detector for the sensor with metal nanoparticles comprises a device for measuring changes in resistance, conductance, alternating current (AC), frequency, capacitance, impedance, inductance, mobility, electrical potential, or voltage threshold.

12. The system according to claim 1, wherein the pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

13. A method of diagnosing, monitoring or prognosing lung cancer or stages or subtypes thereof in a subject or predicting a patient's response to a treatment regimen, the method comprising the steps of:
providing a system according to claim 1;
exposing the apparatus to a test exhaled breath sample;
measuring at least one response induced parameter from the apparatus upon exposure to the test sample to obtain a response pattern; and
analyzing the response pattern obtained in step (c) using a pattern recognition algorithm by comparing it to stored data obtained from a control sample whereby a significantly different response pattern of the test sample as compared the control sample is indicative of lung cancer or stages or subtypes thereof or provides the prediction of a patient's response to a treatment regimen.

14. The method according to claim 13, wherein the response pattern enables to differentiate between subjects having benign solitary pulmonary nodules and subjects having malignant solitary pulmonary nodules; or wherein the response pattern enables to differentiate between subjects having small cell lung cancer and subjects having non-small cell lung cancer; or wherein the response pattern enables to differentiate between subjects having non-small cell lung cancer in an early stage and subjects having non-small cell lung cancer in an advanced stage; or wherein the response pattern enables to differentiate between subjects having adenocarcinoma and subjects having squamous cell carcinoma; or wherein the response pattern enables to differentiate between subjects having lung cancer and subjects having lung metastases.

15. The method according to claim 13, wherein the response pattern is formed by the sensors detection of at least one volatile biomarker which is indicative of lung cancer or stages or subtypes thereof.

16. The method according to claim 15, wherein the at least one volatile biomarker which is indicative of lung cancer or stages or subtypes thereof is 1-octene.

17. The system according to claim 1, wherein the sensors detect at least one volatile biomarker, which is indicative of lung cancer or stages or subtypes thereof.

18. The system according to claim 17, wherein the at least one volatile biomarker which is indicative of lung cancer or stages or subtypes thereof is 1-octene.

19. The system according to claim 17, wherein the either sensors' detection of the at least one volatile biomarker which is indicative of lung cancer or stages or subtypes thereof forms a response pattern, wherein the response pattern enables to differentiate between subjects having benign solitary pulmonary nodules and subjects having malignant solitary pulmonary nodules; or wherein the response pattern enables to differentiate between subjects having small cell lung cancer and subjects having non-small cell lung cancer; or wherein the response pattern enables to differentiate between subjects having non-small cell lung cancer in an early stage and subjects having non-small cell lung cancer in an advanced stage; or wherein the response pattern enables to differentiate between subjects having adenocarcinoma and subjects having squamous cell carcinoma; or wherein the response pattern enables to differentiate between subjects having lung cancer and subjects having lung metastases.

* * * * *